(12) United States Patent
Ries et al.

(10) Patent No.: US 9,362,660 B2
(45) Date of Patent: *Jun. 7, 2016

(54) DOWN THE BORE WITH OPEN WINDOWS AND MANUFACTURING THEREOF

(71) Applicant: Medtronic, Inc., Minneapolis, MN (US)

(72) Inventors: Andrew J Ries, Lino Lakes, MN (US); Jeffrey A Swanson, Cambridge, MN (US); George A Patras, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,035

(22) Filed: Apr. 23, 2015

(65) Prior Publication Data

US 2016/0028181 A1    Jan. 28, 2016

Related U.S. Application Data

(60) Provisional application No. 61/984,385, filed on Apr. 25, 2014, provisional application No. 61/984,367, filed on Apr. 25, 2014.

(51) Int. Cl.
| | |
|---|---|
| *A61N 1/00* | (2006.01) |
| *H01R 13/52* | (2006.01) |
| *A61N 1/05* | (2006.01) |
| *H01R 13/66* | (2006.01) |
| *B29C 45/14* | (2006.01) |
| *B29L 31/00* | (2006.01) |

(52) U.S. Cl.
CPC .......... *H01R 13/5202* (2013.01); *A61N 1/0587* (2013.01); *B29C 45/14639* (2013.01); *H01R 13/665* (2013.01); *B29L 2031/753* (2013.01)

(58) Field of Classification Search
CPC ............................ H01R 24/58; H01R 2201/12
USPC .................. 607/119; 439/669, 909, 668, 667
See application file for complete search history.

(56) References Cited

U.S. PATENT DOCUMENTS

| | | | |
|---|---|---|---|
| 6,799,072 B2 | 9/2004 | Ries et al. |
| 6,817,905 B2 | 11/2004 | Zart et al. |
| 6,895,276 B2 | 5/2005 | Kast et al. |
| 7,155,283 B2 | 12/2006 | Ries et al. |
| 7,164,951 B2 | 1/2007 | Ries et al. |
| 7,231,253 B2 | 6/2007 | Tidemand et al. |
| 7,309,262 B2 | 12/2007 | Zart et al. |

(Continued)

FOREIGN PATENT DOCUMENTS

| | | |
|---|---|---|
| WO | 03075414 A1 | 9/2003 |
| WO | 2009045772 A1 | 4/2009 |

OTHER PUBLICATIONS (PCT/US2015/027664) PCT Notification of Transmittal of the International Search Report and the Written Opinion of the International Searching Authority.

*Primary Examiner* — Phuongchi T Nguyen
(74) *Attorney, Agent, or Firm* — Carol F. Barry

(57) ABSTRACT

An implantable medical device connector assembly and method of manufacture include a molded, insulative shell having an inner surface forming a connector bore, a circuit member including one or more traces extending through apertures in the connector shell. One or more conductive members, positioned along the connector bore, are electrically coupled to the traces. The sealing members are positioned between the conductive members.

19 Claims, 28 Drawing Sheets

(56) References Cited

U.S. PATENT DOCUMENTS

| | | |
|---|---|---|
| 7,317,946 B2 | 1/2008 | Twetan et al. |
| 7,413,482 B2 * | 8/2008 | Ries .................. A61N 1/3752 29/841 |
| 7,526,339 B2 | 4/2009 | Lahti et al. |
| 7,717,754 B2 | 5/2010 | Ries et al. |
| 7,988,497 B2 | 8/2011 | Ries et al. |
| 8,032,221 B2 | 10/2011 | Wengreen et al. |
| 8,062,074 B2 | 11/2011 | Ries et al. |
| 8,065,007 B2 | 11/2011 | Ries et al. |
| 8,123,567 B2 | 2/2012 | Kast et al. |
| 8,190,260 B2 | 5/2012 | Ries et al. |
| 8,206,180 B1 | 6/2012 | Kast et al. |
| 8,401,649 B2 | 3/2013 | Tronnes et al. |
| 8,412,330 B2 | 4/2013 | Kast et al. |
| 8,473,056 B2 | 6/2013 | Engmark et al. |
| 8,628,348 B2 | 1/2014 | Ries et al. |
| 8,700,160 B2 | 4/2014 | Troosters et al. |
| 8,706,229 B2 | 4/2014 | Lahti et al. |
| 8,792,984 B2 | 7/2014 | Kast et al. |
| 8,945,451 B2 | 2/2015 | Ries et al. |
| 2005/0137642 A1 | 6/2005 | Zart et al. |
| 2007/0100386 A1 | 5/2007 | Tronnes et al. |
| 2009/0017700 A1 | 1/2009 | Zart et al. |
| 2009/0266573 A1 | 10/2009 | Engmark et al. |
| 2010/0197174 A1 | 8/2010 | Lahti et al. |
| 2010/0285697 A1 | 11/2010 | Zart et al. |
| 2011/0014807 A1 | 1/2011 | Ries et al. |
| 2011/0190833 A1 | 8/2011 | Ries et al. |
| 2012/0149254 A1 | 6/2012 | Kast et al. |
| 2012/0215296 A1 | 8/2012 | Ries et al. |
| 2013/0218223 A1 | 8/2013 | Ghosh et al. |
| 2013/0226266 A1 | 8/2013 | Murtonen et al. |
| 2013/0307184 A1 | 11/2013 | Ries et al. |
| 2013/0309889 A1 | 11/2013 | Ries et al. |
| 2014/0052225 A1 | 2/2014 | Kast et al. |
| 2014/0123490 A1 | 5/2014 | Ries et al. |

* cited by examiner

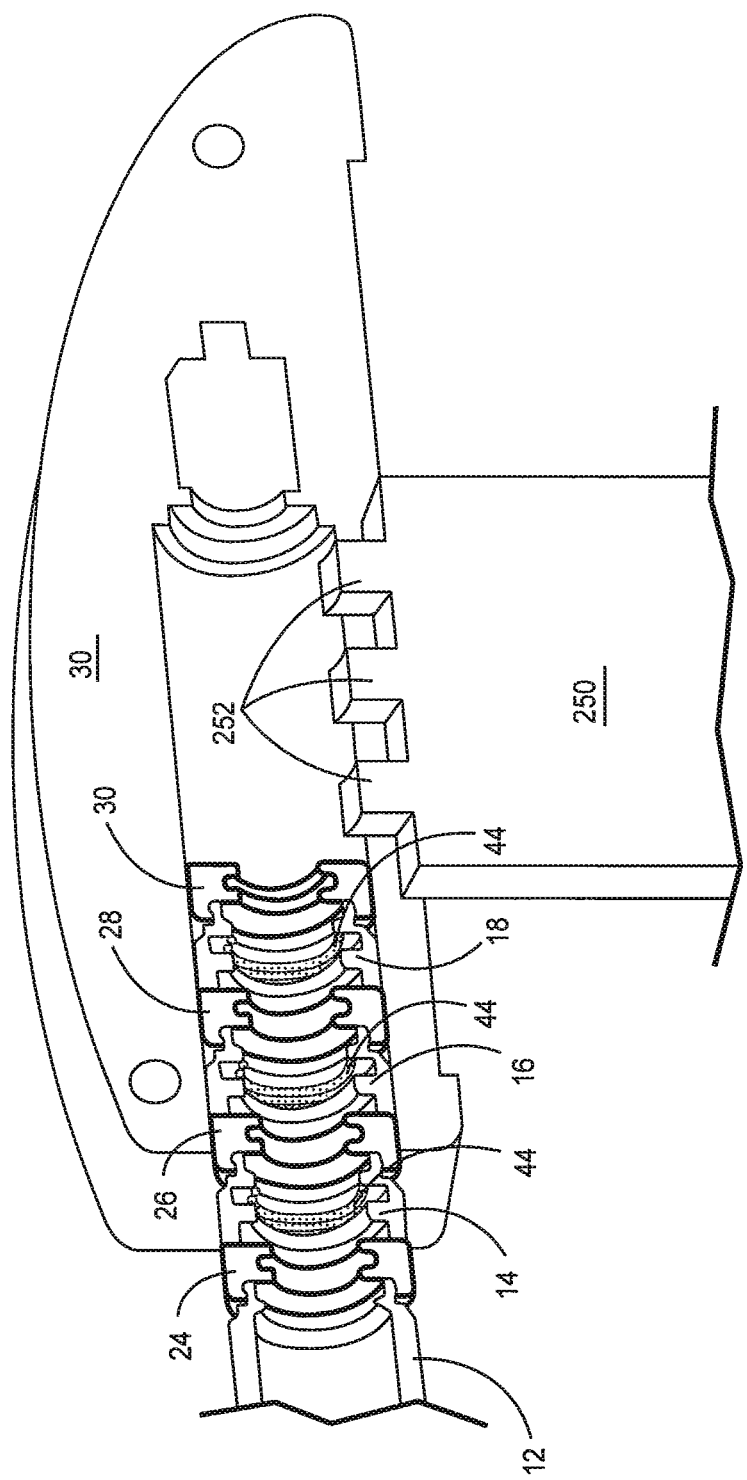

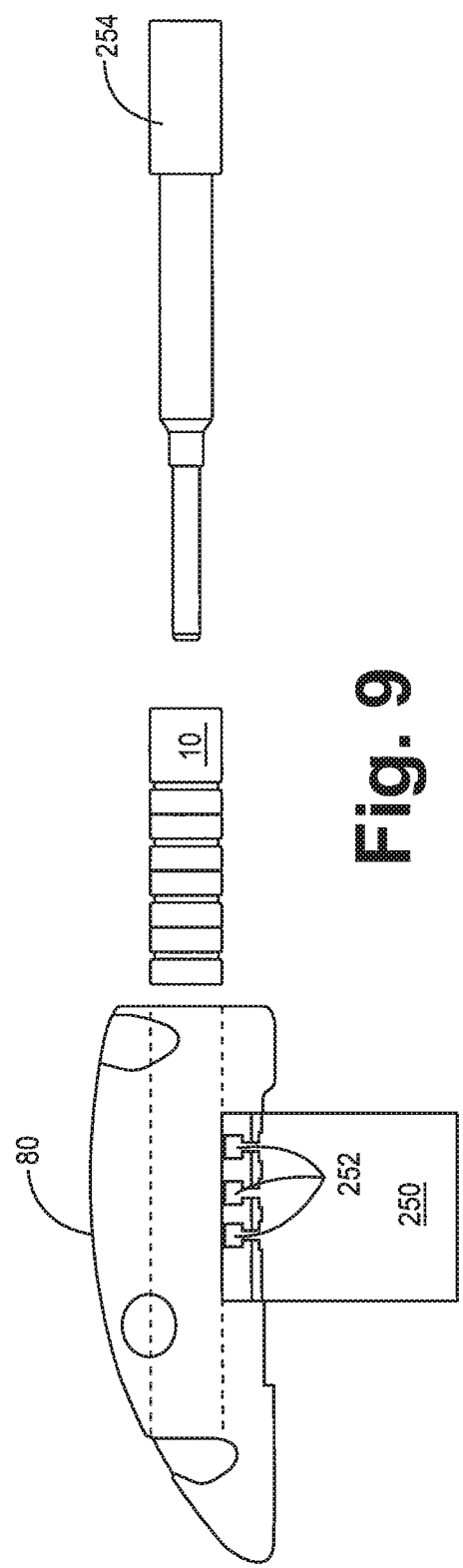

DOWN THE BORE WITH OPEN WINDOWS AND MANUFACTURING THEREOF

CROSS-REFERENCE TO RELATED APPLICATIONS

This application claims the benefit of U.S. Provisional Application Nos. 61/984,367, and 61/984,385 filed on Apr. 25, 2014. The disclosure of the above applications are incorporated herein by reference in its entirety. This application is related to U.S. patent application Ser. No. 14/695,036, filed on the same day entitled "DOWN THE BORE WITH OPEN WINDOWS AND MANUFACTURING THEREOF", herein incorporated by reference in its entirety.

TECHNICAL FIELD

The present disclosure relates generally to implantable medical device connector assemblies, and, more particularly, to a device connector that includes a connector shell with open windows thereby allowing a direct electrical connection between a stacked assembly and an implantable medical device hybrid circuit board.

BACKGROUND

Electrical connectors and other similar electrical components often include electrical conductors embedded within an insulating block to isolate the conductor from the surrounding environment. Embedding the conductor within a block protects the conductor and prevents the delivery of an unintended electrical shock. Electrical connector assemblies are coupled to a hermetically sealed housing of an implantable medical device that encloses internal circuitry such as a hybrid circuit board and one or more batteries. Such a medical device connector assembly is adapted for receiving medical leads used with the implantable medical device.

Methods for forming electrical connector assemblies having conductors embedded within an insulating block may include injection molding techniques or thermoset casting techniques. One method for forming an implantable medical device connector assembly with embedded conductors is generally disclosed in U.S. Pat. No. 6,817,905 (Zart et al.). The method generally includes forming a core portion using either an injection molding process or a machining process. The core portion is fitted with electrically conductive components and submitted to a subsequent overmold process in which a second shot of polymer material is injected into the mold. This process allows complex connector structures to be manufactured in a fast production cycle.

Another exemplary method is described in U.S. Pat. No. 8,628,348, which involves molding a connector shell with a set of closed conductive windows disposed down the bore of the connector shell. The closed conductive windows allows the inner surface of the cylindrical bore to be flush. A stacked subassembly, comprised of seals interleaved with conductive connectors, is then inserted and pushed down the bore while the stacked subassembly remains constrained within the cylindrical bore. Each seal is positioned between closed conductive windows while the conductive connectors are positioned over the conductive windows. A wire, extending from a feedthrough electronic assembly connected to a hybrid board, is then welded to each closed conductive window.

Numerous constructions and assembly methods for implantable medical device connector module assemblies are known in the art, some of which are disclosed in commonly assigned U.S. Pat. Nos. 6,895,276, 7,309,262, 7,317,946, 7,526,339, 7,717,754 and 8,032,221. However, there is still a need for new and improved connector module assembly constructions and associated assembly methods.

BRIEF DESCRIPTION OF THE DRAWINGS

FIG. 8B depicts a schematic view of a mating tool with three prongs that correspondingly fit apertures and project to the proper depth to complete the cylindrical surface of the main bore for the molded shell.

FIG. 9 is a schematic view of a connector shell with a mating tool inserted into apertures with the stacked assembly in position to be inserted down the bore by an insertion tool.

SUMMARY

One or more embodiments of the disclosure involve a method for forming an implantable medical device including a connector assembly adapted to connect to a medical electrical lead. The method comprises providing a circuit member that includes electrical circuitry. A shell is molded using a polymer. The shell includes first and second opposing sides extending between first and second ends thereof. A bore is defined through at least one of the first and second ends of the shell to a bore distal end. A plurality of apertures being defined through at least one of the first and second sides of the shell and disposed along the bore. A stacked subassembly is formed along the connector bore. The stacked subassembly is formed by positioning a first pair of members comprising a first conductive member and a first sealing member along the connector bore. The first conductive member and the first sealing member are positioned together. The first conductive member has a surface exposed through a first aperture of the plurality of apertures disposed in one of the first and second sides of the shell. A second pair of members are positioned together along the bore. The second pair comprises a second conductive member and a second sealing member. The second conductive member has a surface exposed through a second aperture of the plurality of apertures disposed in one of the first and second sides of the shell. A plurality of conductive traces, extending along at least one of the first and second sides of the shell from the circuit member, are coupled to the first and second conductive members through the first and second apertures.

DETAILED DESCRIPTION

In the following description, references are made to illustrative embodiments for carrying out the invention. It is understood that other embodiments may be utilized without departing from the scope of the invention. Unless otherwise indicated, drawing elements are not shown to scale.

Figure 1:
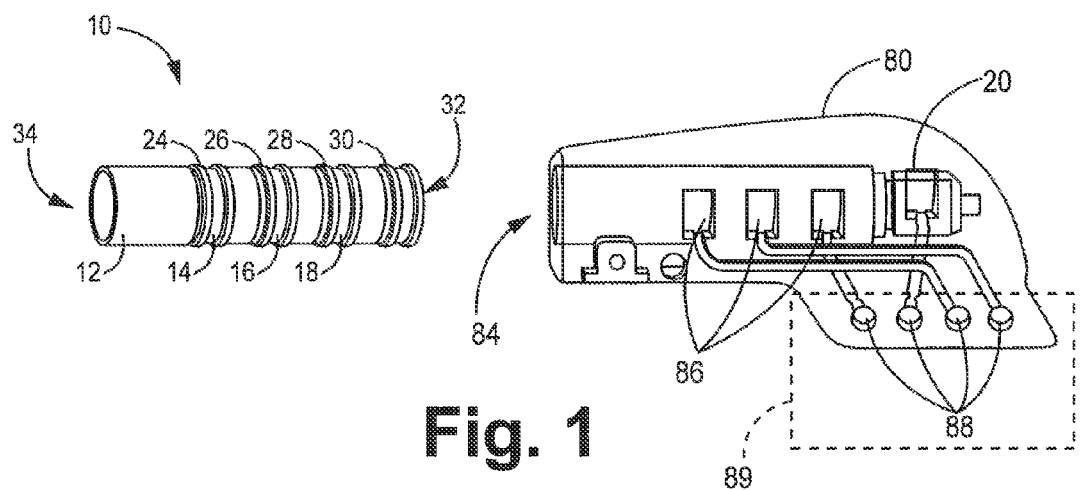
FIG. 1 illustrates a first embodiment perspective view of a stacked subassembly prior to being placed down a bore of a connector shell to form an implantable medical device connector.

The present disclosure is directed to an implantable medical device including a connector assembly adapted for receiving a medical electrical lead. A shell is molded that includes first and second ends with a bore extending therebetween. The shell further includes a plurality apertures or open windows along the bore. A mating tool is moved along the outer surface of the shell and adjacent to the plurality of apertures. The mating tool then contacts and fills the apertures. After the mating tool filled the apertures, the connector bore is flush or substantially flush which allows the stacked subassembly to be positioned in the connector bore. The stacked subassembly comprises a plurality of conductive members with sealing members interleaved between each conductive member (also referred to as contact) after insertion into the bore. Each conductive member is disposed within an aperture of the plurality of apertures formed in the shell to allow electrical connection through the aperture. Additionally, a plurality of sealing members are positioned between the conductive members and between the apertures where the bore diameter is continuous. The mating tool is moved away from the plurality of the apertures in response to the plurality of conductive members being positioned along the connector bore such that the set of conductive members are located within the plurality of apertures. A plurality of conductive traces extending from a circuit member (i.e. hybrid board) are coupled to the plurality of conductive members extending through a side of the shell. Simple single bore designs as shown in FIG. 1 and described herein achieve the highest cost effectiveness compared to other methods. For example, the disclosed method uses less interconnect welds since feedthough wires can be directly placed on conductive connectors members without using additional components or welded interfaces.

FIG. 1 is a perspective view of an exemplary stacked subassembly 10 which is inserted into shell 80 to form an implantable medical device connector assembly. Stacked subassembly 10 includes an end cap 12 and a set of conductive connectors 14, 16, and 18 (also referred to as ferrules or contacts) separated by sealing members 24, 26, 28 and 30. Shell 80, a first embodiment, has a feedthrough that exits from the side of the housing (also referred to as a "can") on a skirt 89 (also referred to as a flange). Connector 20 is adapted for receiving a lead pin terminal 52 and includes an open end aperture 32 through which a pin terminal of a lead connector assembly may be inserted. Connector 20 is shown embodied as a set screw block and further includes a set screw aperture 22 for receiving a set screw (not shown) used for securing the pin terminal of a lead connector assembly to retain the lead connector assembly within a connector bore formed by stacked subassembly 10. Connector 20 may alternatively be embodied as a spring contact or other contact adapted for receiving and engaging a lead pin terminal. The remainder of the connectors 14, 16, and 18 may be embodied as multi-beam contacts, spring contacts, or any other suitable electrical contacts for making electrical connection with lead connector terminals that become aligned with connectors 14, 16, and 18 when the lead connector assembly is fully inserted into stacked subassembly 10. End cap 12 is provided with an open receptacle 34 for receiving a lead connector assembly and acts to terminate the stack. End cap 12 is generally formed of a rigid material which may be conductive or non-conductive.

Sealing members 24, 26, and 28 are fabricated from an insulating material to electrically isolate connectors 14, 16, and 18. Sealing members 24, 26, and 28 are typically formed of a compliant material, such as a medical grade silicone rubber, such that sealing members 24, 26, and 28 form a fluid-resistant seal with insulating structures of a lead connector. When the lead connector is fully inserted into stacked subassembly 10, which has been assembled in an IMD connector assembly, sealing members 24, 26, and 28 are aligned with insulating structures separating lead connector terminals. An inner surface of sealing members 24, 26, and 28 will form a fluid-resistant interface with the insulating structures of the lead connector assembly, thereby preventing body fluids from creating a short circuit between lead terminals and stacked subassembly connectors 14, 16, 18, and 20.

Stacked subassembly 10 can either be pre-assembled or assembled in the bore 84 of the shell 80. Skilled artisans appreciate that the pairs of conductive connector members 14, 16, 18 and seals 24, 26, 28 may be two or more to form a stacked assembly 10. For example, in one or more embodiments, a first pair members, is inserted down the bore 84 such that a first seal member 28 enters the bore 84 first followed by the first conductive connector 18. The first pair of members are positioned at a distal end of the bore 84. The second pair of members, comprising a second seal member 26 enters the bore 84 followed by the second conductive connector 16. The second seal member 26 is adjacent first conductive connector 18. Optionally, a third pair is positioned down the bore 84 such that a third seal member 24 is inserted down the bore 84 followed by the conductive connector 14. The third seal member 24 is adjacent second conductive connector 16. After the first, second and third pairs of conductive connector and seals have been positioned down the bore 84, the end cap 12 is then inserted thereby completing the down the bore 84 assembly.

Stacked subassembly 10 can also be loaded onto an insertion tool and then inserted into the bore 84. An exemplary insertion tool is shown and described in U.S. Pat. No. 7,717, 754 issued Jun. 12, 2008, and assigned to the assignee of the present invention, the disclosure of which is incorporated by reference in its entirety herein. The tip of the insertion tool is used to apply pressure along a surface of stacked subassembly 10 until the stacked subassembly 10 is fully inserted into connector bore 84. In one or more embodiments, it may be beneficial to insert each contact/seal pair individually to ensure accurate position of each contact within each aperture along the bore 84. An adhesive, such as an epoxy, a urethane, a silicone medical adhesive, or other suitable thermoset material, is injected through a fill port to form adhesive bonds between the outer surface of sealing members 24, 26, and 28 and shell inner surface 82. A two-part adhesive may be pre-mixed prior to injection. Examples of suitable adhesives include epoxy and urethane medical application adhesives available from Master Bond, Inc., Hackensack, N.J.

Figure 2:
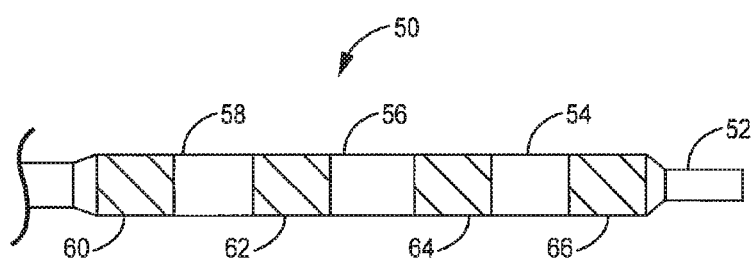
FIG. 2 is a plan view of a proximal lead connector assembly adapted for use with the stacked subassembly of FIG. 1.

FIG. 2 is a plan view of a proximal lead connector assembly 50 adapted for use with the stacked subassembly 10 and shell 80 of FIG. 1. Lead connector assembly 50 includes a pin connector terminal 52 and three ring connector terminals 54, 56, and 58. Lead connector assembly 50 may generally correspond to an IS4 connector assembly, having four inline terminals 52, 54, 56 and 58, however, embodiments of the invention may be adapted for use with other lead connector assembly configurations. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, and 64. Lead connector assembly 50 can be an "in-line" connector assembly or a bifurcated connector assemblies which carry connector terminals on separate branches. In-line lead connector assemblies can have sealing rings along the insulating structures between connector terminals for providing a fluid resistant seal between circuit elements when the lead connector assembly is coupled to an implanted device.

Figure 3:
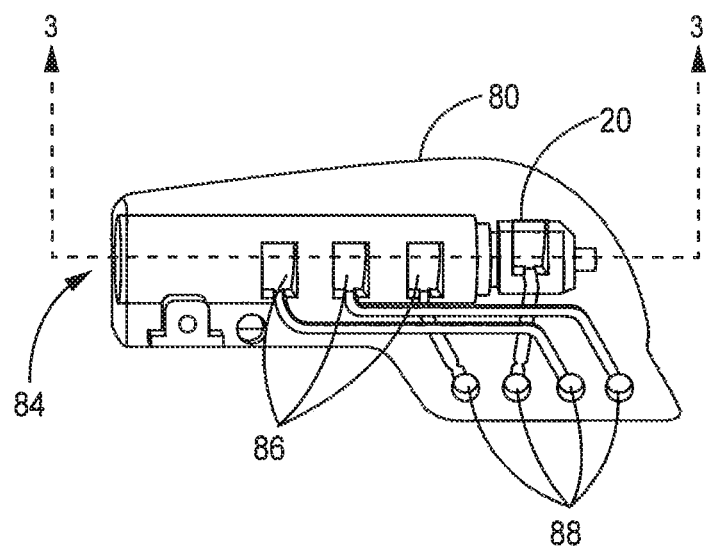
FIG. 3 is an enlarged perspective view of a connector shell including a set of apertures formed therein.
Figure 4:
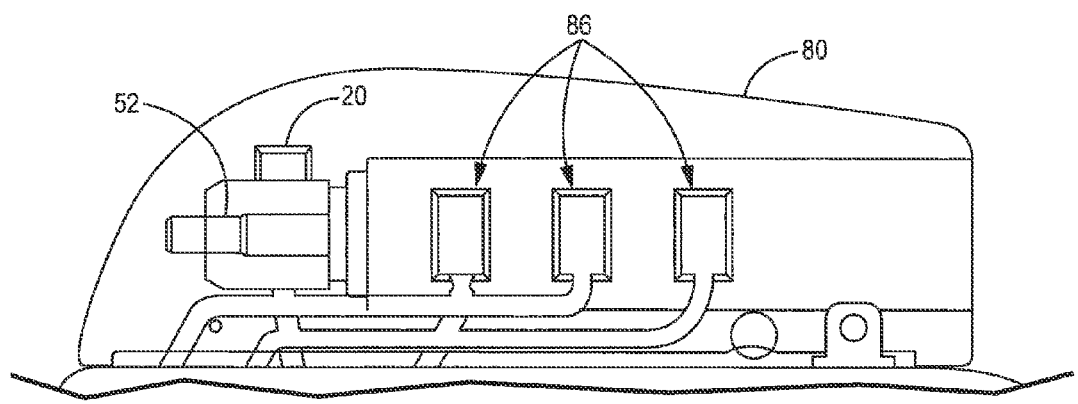
FIG. 4 is a perspective view taken along lines 3-3 of a connector shell including a set of apertures formed therein.
Figure 5:
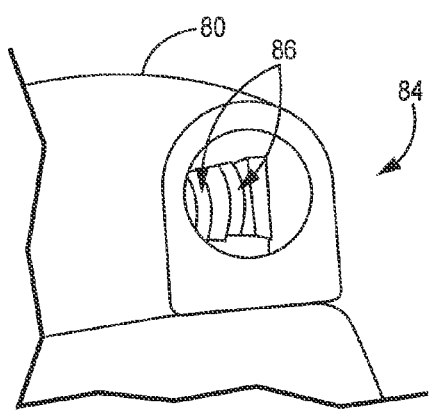
FIG. 5 is an exploded schematic view of apertures formed down a bore of a shell.
Figure 6:
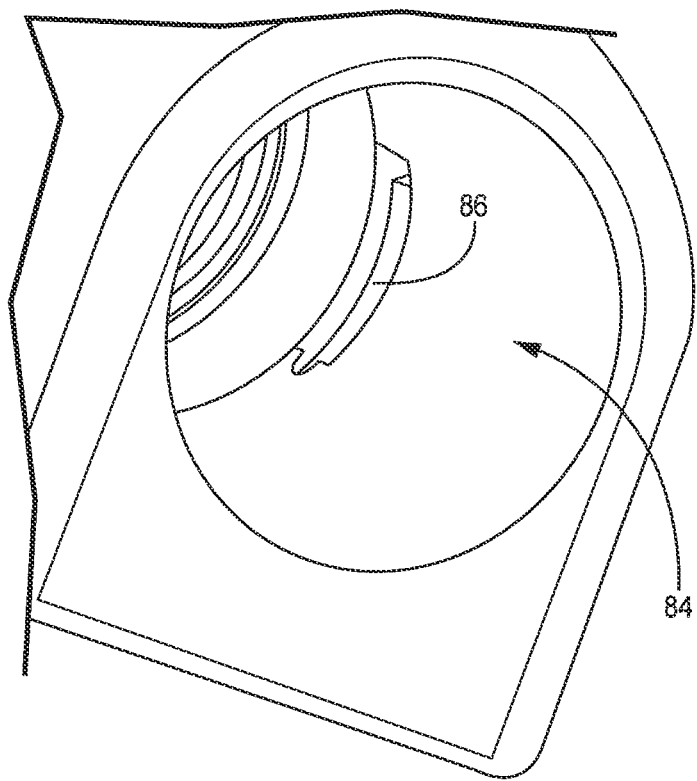
FIG. 6 is an exploded schematic view of apertures formed down the bore of the shell.
Figure 7A:
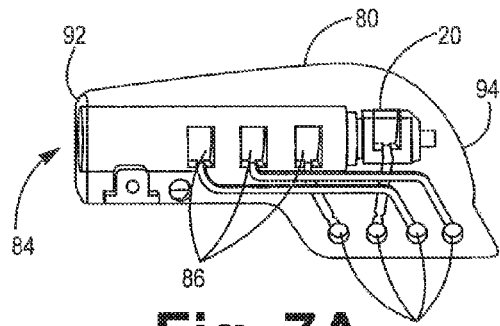
FIG. 7A depicts a molded shell that includes first and second ends with a bore extending therebetween.
Figure 7B:
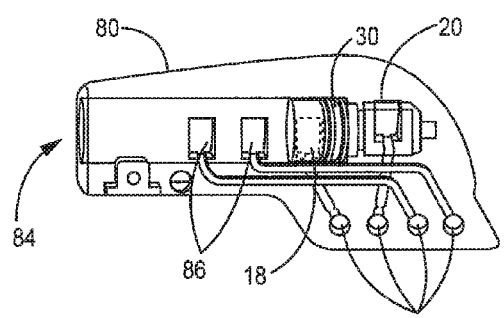
FIG. 7B depicts a molded shell after one pair comprising a first conductive member and a first sealing member that is inserted down the bore.
Figure 7C:
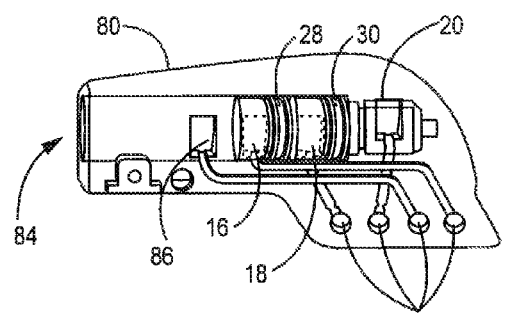
FIG. 7C depicts a molded shell after a second pair comprising a second conductive member and a second sealing member that is inserted down the bore.
Figure 7D:
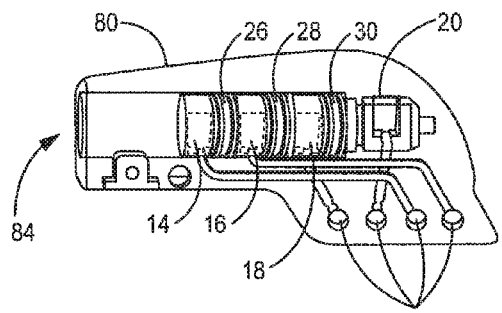
FIG. 7D depicts a molded shell after a second pair comprising a second conductive member and a second sealing member that is inserted down the bore.
Figure 7E:
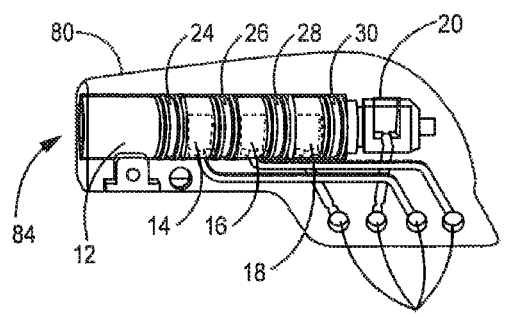
FIG. 7E depicts a molded shell after a third pair comprising a third conductive member and a third sealing member that is inserted down the bore.

FIG. 3 is a perspective view of shell 80 and FIG. 4 is a top view of a lead connector assembly 50 inserted into a connector assembly shell according to one or more embodiments of the invention. Shell 80 is formed during a single shot casting or molding process. A single shot of molding material means that solely one molding operation and one shot of polymer or mixtures of polymers is used at a single time. An exemplary description of how a molding process is performed is disclosed in U.S. Pat. No. 6,817,905 (Zart et al.), hereby incorporated herein by reference in its entirety; however, one or more embodiments of the present disclosure does not include the overmolding process that is disclosed in Zart. Shell 80 may be formed from a polymer, such as a polyurethane, and may thus be formed during high pressure and/or high temperature processes. Suitable polyurethane materials for forming shell 80 include a 75D polyurethane such as Thermedics™ Tecothane® available from Noveon, Inc., Cleveland, Ohio, or Pellethane™ available from Dow Chemical, Midland, Mich. Thermoset epoxy materials can also be used. Shell 80 is fabricated by loading a mandrel (not shown) in a mold into which the polymer material is applied. Shell 80 is thereby formed having an inner surface 82, which is formed by the mandrel, defining a connector bore 84. Shell 80 may be additionally formed with channels 88, grooves, recesses or other features for receiving, retaining and/or aligning conductive traces of circuit member 90. In one or more embodiments, shell 80 is formed without a permanent metal molded therein. In one or more other embodiments, shell 80 may include embedded components or be formed with other additional features for receiving components during an assembly process, depending on the particular application. For example, the set screw block may be formed in shell 80.

As shown in FIGS. 3 and 4, shell 80 includes connector bore 84, however it is recognized that a connector shell 80 may be formed having multiple connector bore 84 to allow connection of more than one lead to the associated IMD. Shell 80 is formed having a plurality of apertures 86 (i.e. open windows) aligned with traces 92 extending from circuit member (i.e. hybrid board) (not shown). Apertures 86, become filled with conductive connectors 14, 16, and 18 provide access for electrically coupling traces 92 to connectors included in the stacked assembly 10 positioned in connector bore 84. Shell 80 further includes a fill port (not shown) used for delivering an adhesive for creating a bond between shell inner surface 82 and sealing members included in a stacked subassembly inserted in connector bore 84. An over fill port (not shown) is provided to allow excess adhesive and air bubbles to escape during the delivery process.

Figure 12:
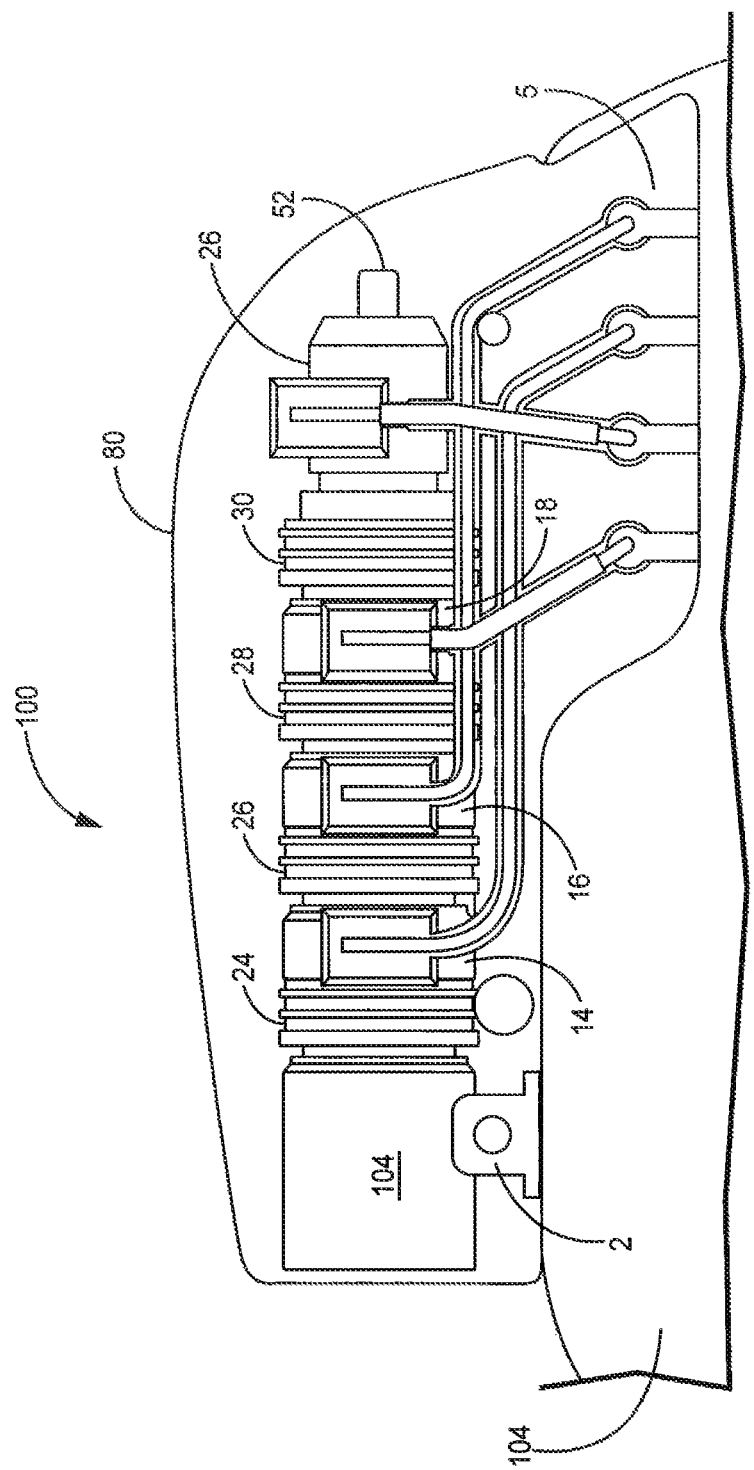
FIG. 12 is a perspective view of a device connector assembly including a molded shell and stacked subassembly inserted into the bore of the molded shell.

Referring to FIGS. 3-6, open windows or apertures 86 are molded into shell 80. The dimensions of each aperture is 1-5 millimeters (mm)×1-5 mm with a depth of 0.5-5 mm. Open windows 86 are configured to receive connectors 14, 16, 18, which allow access for electrically coupling circuit member traces 92 to each of connector members 14, 16, 18. For example, as shown in FIG. 12, traces 92 maybe laser welded to connector members 14, 16, 18 through open windows 86. Windows 86 are subsequently filled with an insulating adhesive, such as silicone rubber to prevent ingress of body fluids around the circuit member connections. Alternatively, a conductive adhesive may be applied through windows 86 in order to electrically couple traces 92 to connector members 14, 16, 18 and set screw block 20. An insulating adhesive may then be applied over the conductive adhesive to seal windows 86.

In still another embodiment, traces 92 and connector members 14, 16, 18 are mechanically coupled to provide electrical connection between the traces and the connector members. For example, traces 92 may be pressed, staked, crimpled, or riveted to connector members 14, 16, 18 and 20 through windows 86. Any suitable method for electrically coupling traces 92 to connector members 14, 16, 18 may be used. Electrical connection of traces 92 with connector members 14, 16, 18 may occur before or after forming adhesive bonds.

Figure 10:
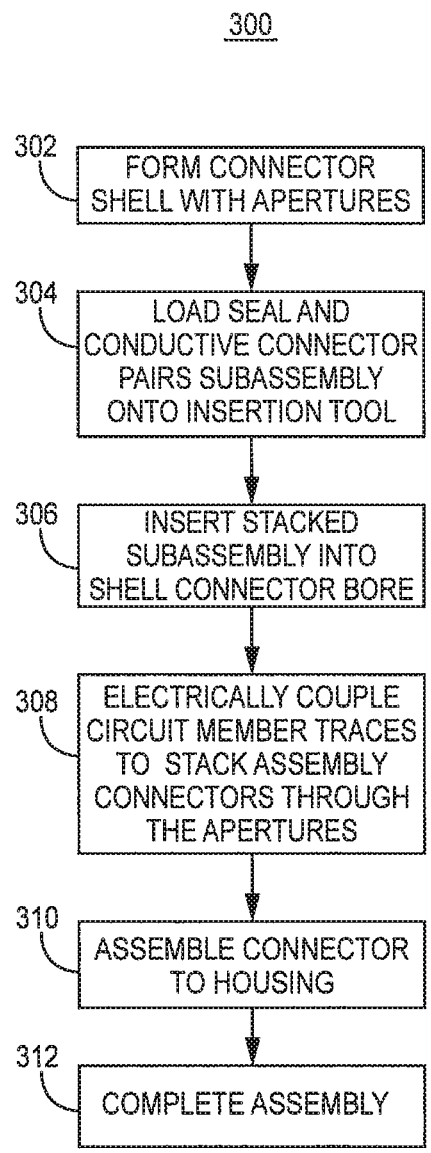
FIG. 10 is a flow chart for a method of inserting a stacked assembly into a connector shell with a set of apertures that allows conductive connectors to be electrically connected with a feedthrough assembly.

The flow chart of FIG. 10 describes the formation of a connector assembly for use in an implantable medical device while FIGS. 7A-7E provide cross-sectional views of connector shell 80 as each operation is performed in order to form the connector assembly. Method 300 includes assembling a mandrel in a mold for forming a connector shell at block 302. Typically, the shell 80 is comprised of one or more polymer materials such as polyurethane in a high temperature, high pressure process. A shell inner surface 82 is formed by the mandrel defining a connector bore 84.

The connector shell 80 is molded at block 304 using a one shot molding process. The one shot molding process employs one or more polymers that is used during a single run of the molding machine. In one or more embodiments, an overmold process is not used. The molded shell, shown in FIG. 7A, includes first and second ends 92, 94 with a bore 84 extending between the first and second ends 92, 94. In one or more embodiments, the plurality of apertures 86 are radially disposed along the bore 84 and extend through the connector shell wall 96. The apertures 86 are spaced apart from each other. Apertures 86 serve the purpose of allowing the conductive lines or traces extending from a feedthough assembly to pass through the apertures 86 to the conductive connector members 14, 16, 18 of a stacked assembly 10.

The shell 80 may further include other features such as a fill port for injecting adhesive for bonding the shell inner surface 82 with the outer surface of sealing members positioned in the connector bore 84, set screw apertures, and other features for accommodating additional connector bore 84 circuit members, connectors, or other components to be included in the connector assembly.

Figure 8A:
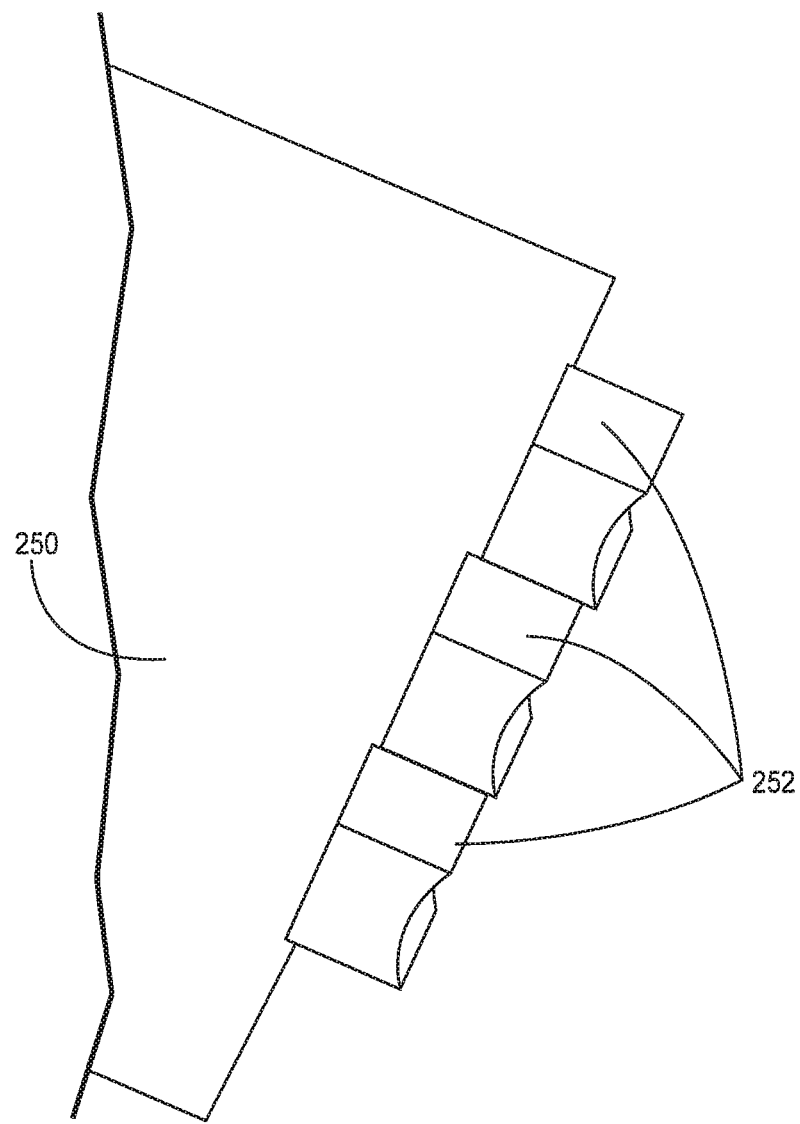
FIG. 8A depicts a schematic view of a mating tool with three prongs that correspondingly fit apertures and project to the proper depth to complete the cylindrical surface of the main bore.

Optionally, a mating tool 250 is used with either the first or second embodiments of shells such that the mating tool 250 is moved over the shell 80 until the mating tool head is adjacent to the plurality of apertures at block 306. The mating tool 250 can be used to plug the apertures 86 to further assist seals to more easily move over or across the open windows 86 without the seals being deleteriously affected. Skilled artisans will appreciate that the mating tool 250 is not required to place or position pairs of sealing and conductive members down the bore 84. An exemplary mating tool 250 is shown in FIGS. 8A-8B. While mating tool 250 is depicted as a body with two rectangular shaped prongs 252 or protruding members extending from the body, skilled artisans understand that a shell connector 80 that includes three apertures 86 requires a mating tool 250 with three prongs to corresponding fit apertures 86 and project to the proper depth to complete the cylindrical surface of the main bore 84.

At block 308, a stacked subassembly is formed along the connector bore 84 by inserting pairs of members down the bore 84 as shown and described relative to FIG. 7. Each pair comprises a first conductive member and a first sealing member. The pair are moved together such that the conductive member has a surface exposed by an aperture or window formed in the shell. After one pair is inserted down the bore 84, another pair is inserted down the bore 84. More specifically, the stacked subassembly is formed by positioning a first pair (FIG. 7B), second pair (FIG. 7C), and third pairs (FIG. 7D), of conductive connector members 14, 16, and 18 interleaved with sealing members 24, 26, 28 along the connector bore 84 such that the conductive member is disposed within an aperture 86. In one or more embodiments, each pair includes a sealing member and a conductive member that interlock together. Each conductive connector member 14, 16, and 18 of each pair is disposed within an aperture 86. End cap 12 is then inserted down the bore 84 as shown in FIG. 7E. A fluid-resistant interface is formed between the outer surface of the sealing members and the inner surface of the connector shell 86 via the compressed state of the sealing member outer diameter against the inner surface 82 of bore 84.

Figure 8C:
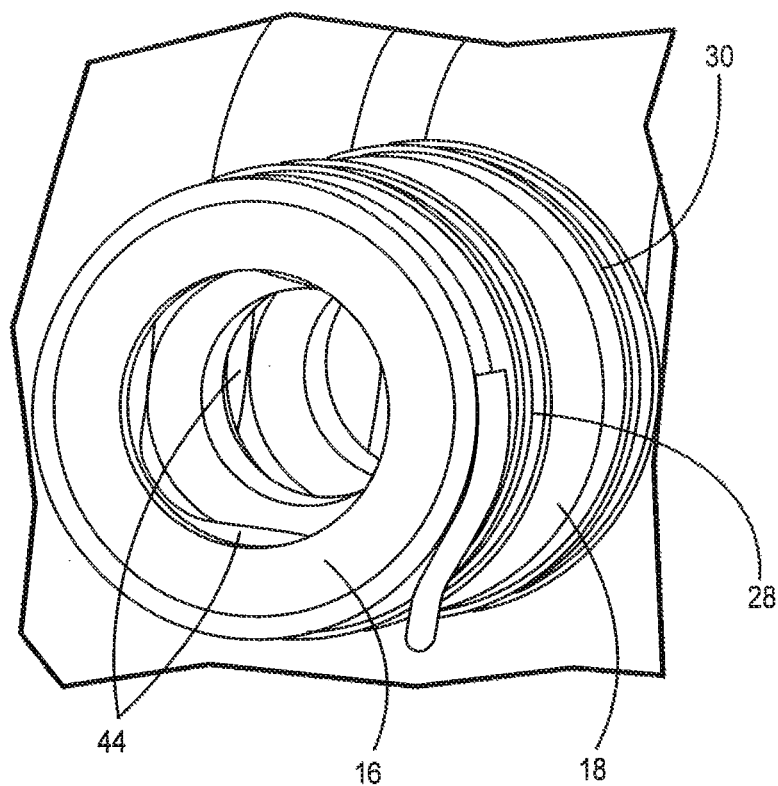
FIG. 8C is an enlarged schematic view down the bore depicting pairs comprised of a seal member and a conductive member with a conductive clip disposed along an inner surface of each conductive member.

FIG. 8C depicts a conductive clip 44 disposed within each of the conductive connector members 14, 16, and 18. Conductive clip can be formed in one or more conductive pieces. An exemplary conductive clip is shown and described in U.S. Pat. No. 8,706,229 issued Apr. 22, 2014, and assigned to the assignee of the present invention, the disclosure of which is incorporated by reference in its entirety herein.

In one or more other embodiments, stacked subassembly 10 is separately formed and then inserted into bore 84. For example, stacked subassembly 10 including sealing members, connectors and an end cap, which may be provided with interlocking features, are loaded onto an insertion tool 254. Using the insertion tool 254, the stacked subassembly is inserted into the shell connector bore 84, as is shown in FIG. 9. Retention members (not shown) may be provided along the stacked subassembly outer diameter for engaging the shell inner surface 82 and securing the stacked subassembly 10 within the connector bore 84 upon full insertion. A second insertion tool may be used to compress the stacked subassembly within the connector bore 84.

After the stacked assembly is down the bore 84, the optional mating tool 250 can then be moved away from the plurality of the apertures 86 in response to the plurality of conductive members being positioned along the connector bore 84 such that each conductive member is located within an aperture 86. A plurality of wires 46 (also referred to as conductive traces) extending from a circuit member are coupled to the plurality of conductive members extending through a side of the shell.

The circuit member traces are electrically coupled to stack assembly 10 conductive connector members 14, 16, and 18 through the windows or apertures 86 that leaves a portion of the surface of the conductive connector members 14, 16, and 18 exposed. The exposed surface of the conductive connector member 14, 16, and 18 is electrically connected to the circuit through the traces 92. Electrical coupling between circuit member traces and conductive connector members 14, 16, 18 may involve welding, or application of conductive adhesives. Electrical coupling between traces and connectors may additionally or alternatively include mechanical coupling between the traces and connectors involving riveting, staking, crimping or a protruding mechanical coupling member such as a spring, barb, button, or beam.

Figure 11:
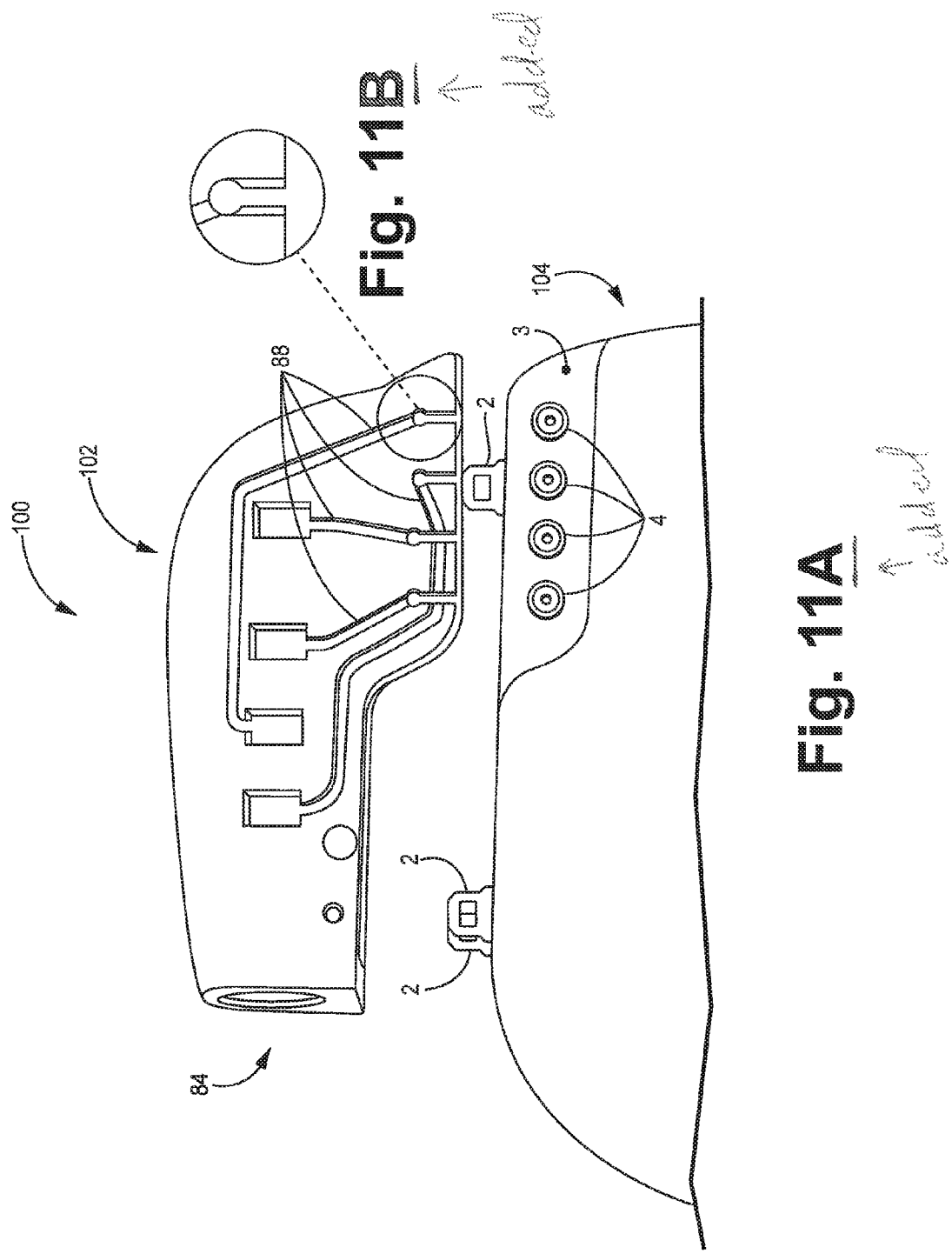
FIG. 11A is a perspective view of a connector assembly positioned over the can prior to the connector assembly being attached with pins to the can.
FIG. 11B is an exemplary key hole slot channel.

The connector assembly 102 is assembled with housing 104 to form implantable medical device (IMD) 100 at block 314, as is shown in FIG. 11. The connector assembly 102 is placed over the housing 104 (also referred to as the device case or can). In particular, the implantable medical device connector assembly 102 is secured to the housing 104.

Wires 46 are connected to cover 48. Cover 48 comprises the same or different conductive material as wire 46. Cover 48 is depicted as rectangular in shape but can be configured as any shape provided that cover 48 covers aperture 86. Wires 46 are routed via grooves 88 and the wire 46 is then welded (e.g. hot welded such as spot welded, cold welded) to wire 44. The connector assembly 102 is pinned in place to the housing 104. Weld tab 2 helps to mechanically hold or secure the connector assembly 102 to the housing 104. The feedthrough wires are either brazed to feedthrough insulators 4 or glassed in. Feedthrough insulators 4 isolate the feedthrough wires electrically from the device case, while also providing a hermetic seal for IMD 100.

FIG. 12 is a cut-away perspective view of a device connector assembly including a molded shell 80 and stacked subassembly 10 formed down the bore 84 of the molded shell 80. As previously described, connector assembly 102 includes molded shell 80 formed during a molding process that includes windows or apertures 86 to allow circuit member traces to directly connect with conductive connector members of the stacked assembly 10. A stacked subassembly 10 is inserted into connector bore 84 having receptacle in end cap 12 for receiving a lead connector assembly. The stack assembly 10 may be inserted in sections (e.g. one or two pairs of seal members and conductive connector members) to better control the position of each contact. In an alternative embodiment, the stack assembly 10 can be pre-assembled and then positioned within bore 84 through a single insertion. Connector assembly 102 may further include one or more additional receptacles for receiving additional leads in one or more additional connector bore 84. Connector assembly 102 includes a set screw aperture for receiving a set screw advanced into a set screw block positioned along connector bore 84. Connector assembly 102 may include additional set screw apertures as needed for receiving additional set screws used for securing lead connector assemblies positioned in other connector bore 84. Connector assemblies may alternatively be fabricated with other connectors in place of set screw blocks, such as spring connectors, for receiving lead connector pins, thereby eliminating the need for set screw apertures.

Figure 13:
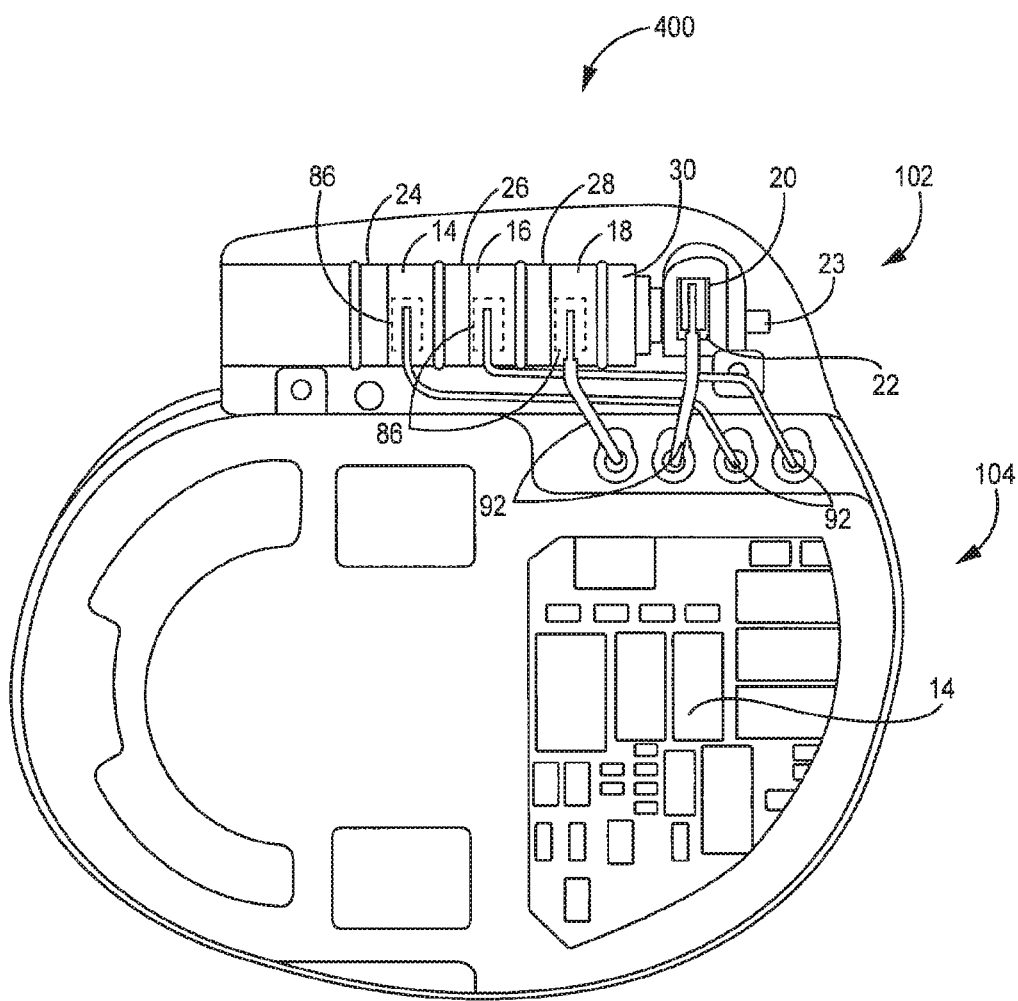
FIG. 13 is a perspective view of the completed connector assembly coupled to an implantable medical device (IMD).

FIG. 13 is a perspective view of the completed connector assembly 102 shown in FIG. 12 coupled to housing 104 to form an IMD 400. IMD 400 may be a pacemaker, cardioverter/defibrillator, neurological stimulator, physiological monitor, or any other implantable medical device utilizing medical leads. In particular, sealing members are provided along a stacked subassembly 10 for creating a fluid-resistant seal with insulating portions of a lead connector assembly inserted into a receptacle. The sealing members also form a fluid-resistant interface with the inner surface of shell 86 along the outer surface of the sealing members. Stacked subassembly 10 is assembled with or without an insertion tool and inserted in connector shell 86 after shell 86 has been molded. The circuit member (also referred to as a hybrid board), partially embedded in connector shell (not shown), may be trimmed and electrically connected to internal circuitry enclosed in IMD housing. Electrical connection between IMD internal circuitry (not shown) and the circuit member is typically made via a feedthrough array extending through hermetically sealed housing.

Figure 14:
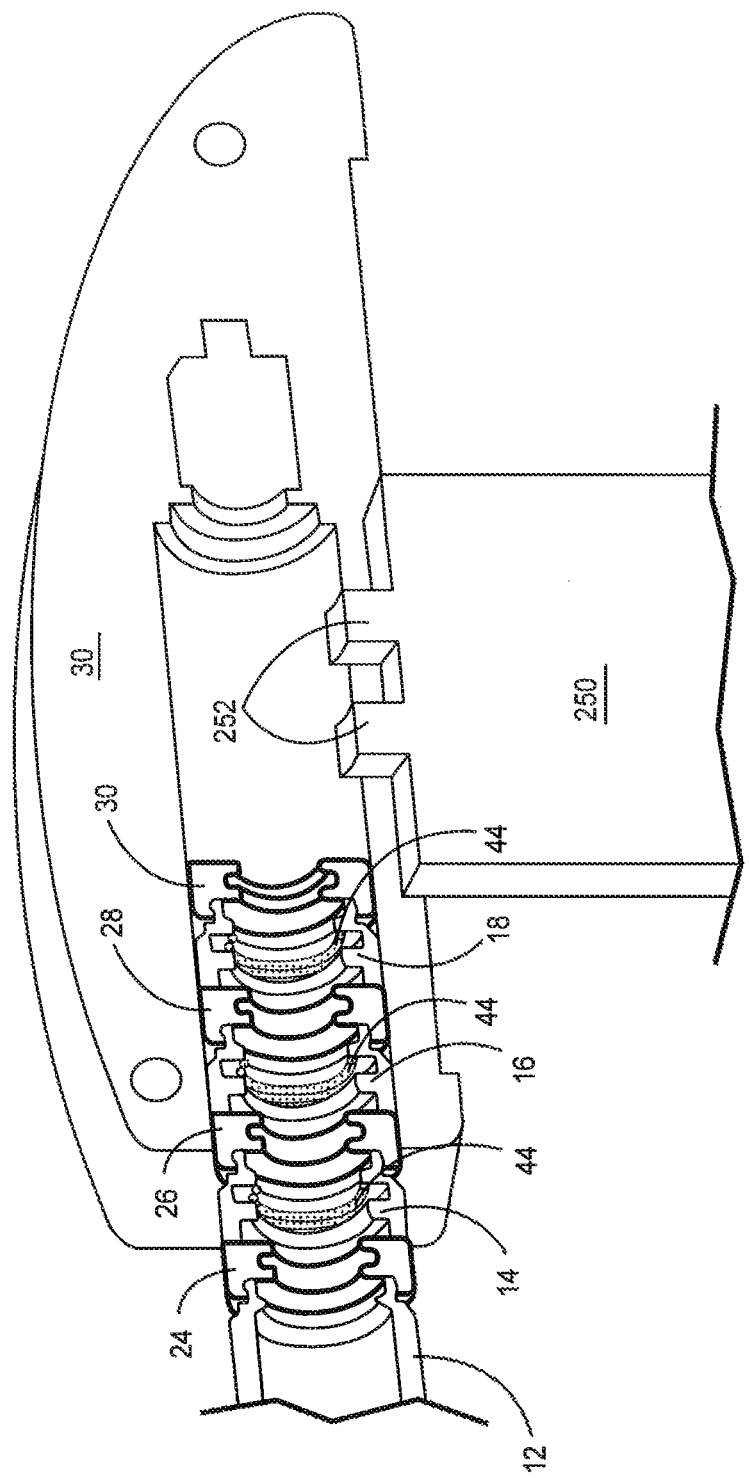
FIG. 14 is a schematic view of a mating tool used to fill apertures in a connector shell so that the inner surface down the bore of the connector shell is substantially flush.

While the present disclosure has been described with molded shell 80 including three apertures 86 or open windows, skilled artisans appreciate that shell 80 could be molded with only two apertures 86. Accordingly, only two pairs of conductive connector members and sealing members would be used in stacked assembly 10. The mating tool would be configured to include two protruding prongs, shown in FIG. 14, to cover apertures 86 in order to allow the pairs to be easily inserted down the bore 84. From this stacked assembly 10, each conductive connector member would fit into a single aperture 86. Thereafter, wire 46 and cover 48 would be connected to wire 44.

Figure 15:
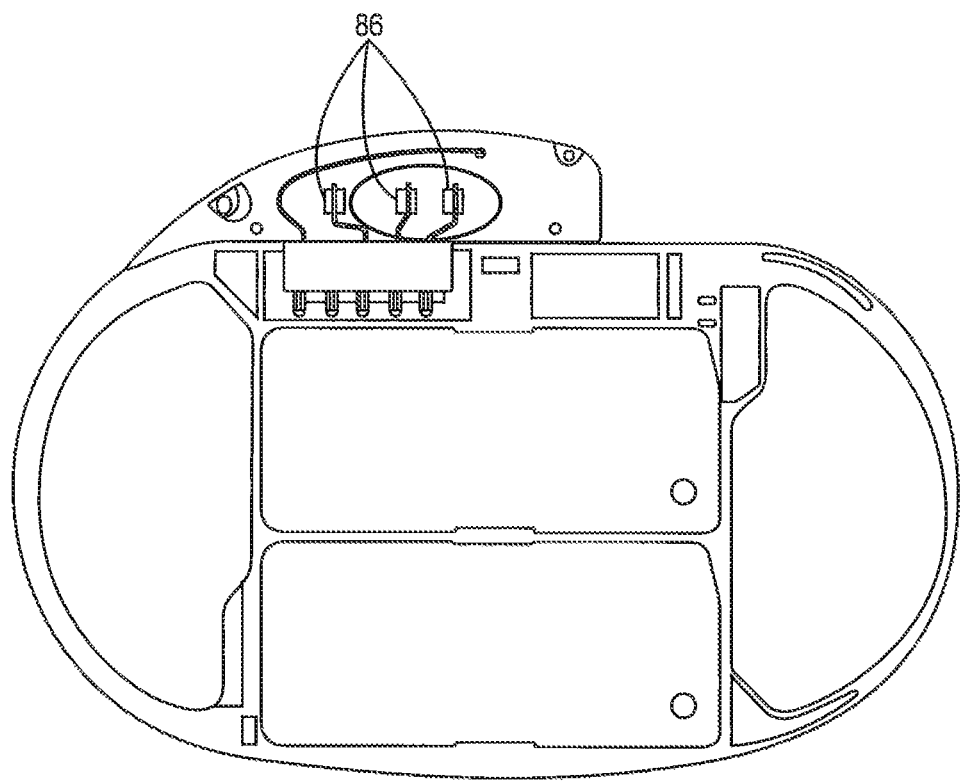
FIG. 15 is a perspective view of yet another completed connector assembly coupled to an IMD.

FIG. 15 is a perspective view of yet another completed connector assembly coupled to the housing 104 to form an IMD. The IMD may be a pacemaker, a cardiac resynchronization therapy pacemaker, a cardioverter/defibrillator, neurological stimulator, physiological monitor, or any other implantable medical device utilizing medical electrical leads. The completed connector assembly can be optionally formed solely using the two prongs extending from the mating tool of FIG. 14 so that the connector bore 84 is flush within the bore 84 while the pairs of connector members and sealing members are slid down the bore 84. Stacked subassembly 10 is assembled with or without an insertion tool and inserted in connector shell 86 after shell 86 has been molded. The circuit member (also referred to as a hybrid board), partially embedded in connector shell (not shown) includes legs that, may be trimmed and electrically connected to internal circuitry enclosed in IMD housing. Trimmed means that the legs are cut-off from the board. Electrical connection between IMD internal circuitry (not shown) and the circuit member is typically made via a feedthrough array extending through hermetically sealed housing.

FIGS. 16-25 involve a second embodiment of an implantable medical device connector assembly 500 adapted for receiving one or more medical electrical leads. FIGS. 16A-16B depict perspective views of a stacked subassembly prior to being placed down a bore of a connector shell 502 to form an implantable medical device connector. Connector assembly 500 comprises shell 502 and stacked assembly 10, which is inserted into an elongated bore 530a. After the stacked assembly is positioned within bore 530a, the left ventricular medical electrical lead is inserted through the elongated lumen formed by the stacked assembly 10. Elongated bores 530b-c are also configured to receive medical electrical leads such as the right ventricular medical electrical lead and the atrial medical electrical lead, respectively.

Shell 502 further includes first, second and third sides 504, 506, and first, second and third ends 510, 512, and 514, respectively. First and second sides 504, 506 extend between first, second and third ends 510, 512, 514, respectively, thereby forming a substantially V-shaped body. First and second sides 504, 506 comprise a substantially larger surface area than any one of first, second and third ends 510, 512, 514. First and second sides 504, 506 are diametrically opposed from each other. Shell 502 is formed without the skirt 89 that is shown in shell 80. First side 504 shows a plurality of grooves or channels 502, 522a,b, 524a-c, 526a,b configured to receive conductive feedthroughs, wires or traces to connected with electronic components.

Groove 503 is configured to receive a conductive wire such as an antenna. The antenna 544a has a proximal end that is electrically and mechanically directly connected (e.g. soldered etc.) to a hybrid, seated on an insulator cup (not shown), while the distal end of the antenna is free floating or not directly electrically connected to any other electrical element.

Grooves 522a,b are configured to receive conductive wire or feedthroughs to the RV and LV tip electrodes, respectively. Grooves 524a-c, are configured to receive wires or feedthroughs for the left ventricular ring electrodes such as LVR1, LVR2, and LVR3. Grooves 526a,b are configured to receive wires or feedthroughs the RV ring and the atrial ring, respectively. Several differences exist between shell 80 of the first embodiment and shell 502 of the second embodiment. For example, shell 80 includes a skirt 89 while shell 502 lacks a skirt. Another difference is that shell 80 has a feedthrough that exits from the side of the can on a ledge 89 shell 502 the feedthrough exits from the top. FIG. 11 clearly shows that the feedthrough would exit straight out or perpendicular to the face (i.e. larger surface area) of the device.

Stacked subassembly 10 includes an end cap 12 and a set of conductive connectors 14, 16, and 18 (also referred to as ferrules or contacts) separated by sealing members 24, 26, 28 and 30. Connector 20 (also referred to as a set block) is adapted for receiving a lead pin terminal 52 and includes an open end aperture 32 through which a pin terminal of a lead connector assembly may be inserted. Connector 20 is shown embodied as a set screw block and further includes a set screw aperture 22 for receiving a set screw (not shown) used for securing the pin terminal of a lead connector assembly to retain the lead connector assembly within a connector bore 530c formed by stacked subassembly 10. Connector 20 may alternatively be embodied as a spring contact or other contact adapted for receiving and engaging a lead pin terminal. The remainder of the connectors 14, 16, and 18 may be embodied as multi-beam contacts, spring contacts, or any other suitable electrical contacts for making electrical connection with lead connector terminals that become aligned with connectors 14, 16, and 18 when the lead connector assembly is fully inserted into stacked subassembly 10. End cap 12 is provided with an open receptacle 34 for receiving a lead connector assembly and acts to terminate the stack. End cap 12 is generally formed of a rigid material which may be conductive or non-conductive.

Sealing members 24, 26, and 28 are fabricated from an insulating material to electrically isolate connectors 14, 16, and 18. Sealing members 24, 26, and 28 are typically formed of a compliant material, such as a medical grade silicone rubber, such that sealing members 24, 26, and 28 form a fluid-resistant seal with insulating structures of a lead connector. When the lead connector is fully inserted into stacked subassembly 10, which has been assembled in an IMD connector assembly, sealing members 24, 26, and 28 are aligned with insulating structures separating lead connector terminals. An inner surface of sealing members 24, 26, and 28 will form a fluid-resistant interface with the insulating structures of the lead connector assembly, thereby preventing body fluids from creating a short circuit between lead terminals and stacked subassembly connectors 14, 16, 18, and 20.

Stacked subassembly 10 can either be pre-assembled or assembled in the bore 530a of the shell 502. Skilled artisans appreciate that the pairs of conductive connector members 14, 16, 18 and seals 24, 26, 28 may be two or more to form a stacked assembly 10. For example, in one or more embodiments, first pair, comprising conductive connector 18 and first seal member 28, is positioned down the bore 530a. First seal member 28 enters the bore 530a before the conductive connector 18 enters the bore 530a. The second conductive connector 16 and the second seal member 26 pair is inserted down the bore 530a such that seal member 26 is positioned next to first conductive connector 18. Optionally, a third conductive connector 14 and a third seal member 24 pair is inserted down the bore 530a. After the paired conductive connector and seals have been positioned down the bore 530a, the end cap 12 is then inserted thereby completing the down the bore 530a assembly.

Stacked subassembly 10 can also be loaded onto an insertion tool and then inserted into the bore 530a. An exemplary insertion tool is shown and described in U.S. Pat. No. 7,717,754 issued Jun. 12, 2008, and assigned to the assignee of the present invention, the disclosure of which is incorporated by reference in its entirety herein. The tip of the insertion tool is used to apply pressure along a surface of stacked subassembly 10 until the stacked subassembly 10 is fully inserted into connector bore 530a. In one or more embodiments, it may be beneficial to insert each contact/seal pair individually to ensure accurate position of each contact within each aperture along the bore 530a. An adhesive, such as an epoxy, a urethane, a silicone medical adhesive, or other suitable thermoset material, is injected through a fill port to form adhesive bonds between the outer surface of sealing members 24, 26, and 28 and shell inner surface 82. A two-part adhesive may be premixed prior to injection. Examples of suitable adhesives include epoxy and urethane medical application adhesives available from Master Bond, Inc., Hackensack, N.J.

Figure 16A:
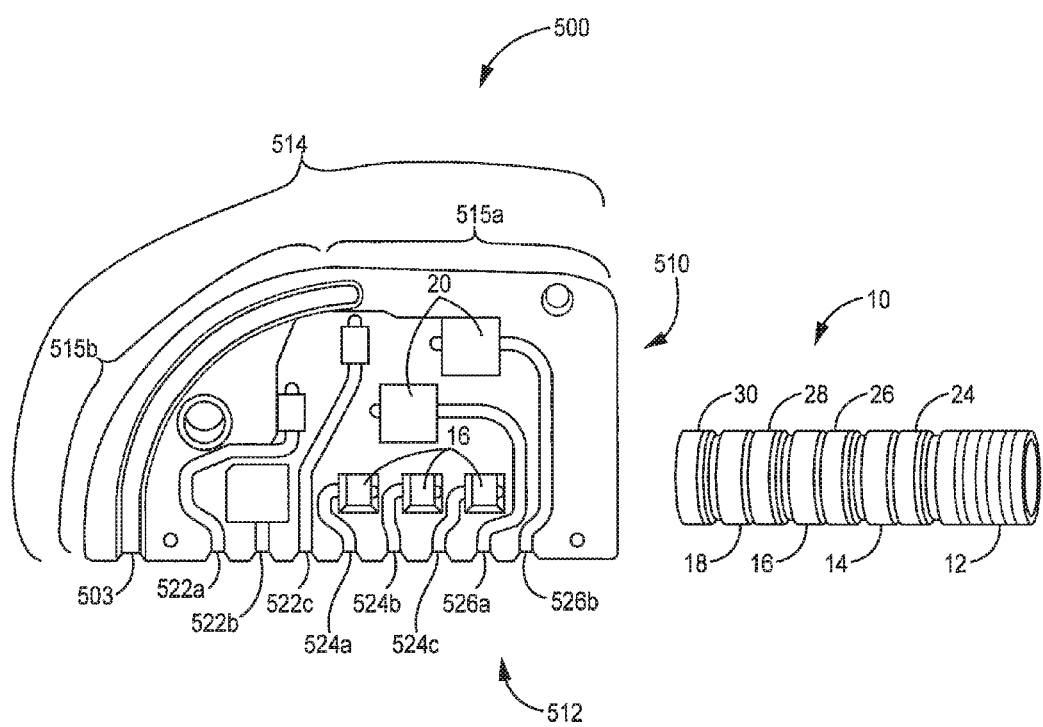
FIG. 16A illustrates a second embodiment perspective view of a stacked subassembly prior to being placed down a bore of a connector shell to form an implantable medical device connector.
Figure 16B:
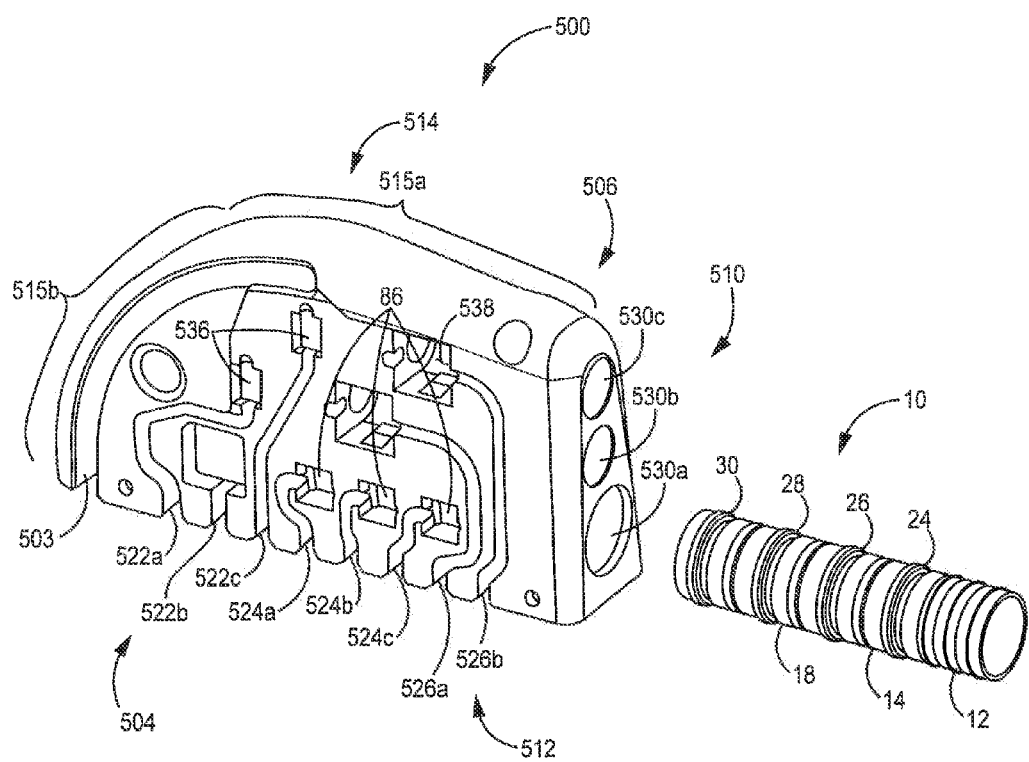
FIG. 16B illustrates an angled perspective view of the stacked subassembly, shown in FIG. 16A, prior to being placed down a bore of a connector shell to form an implantable medical device connector.
Figure 17:
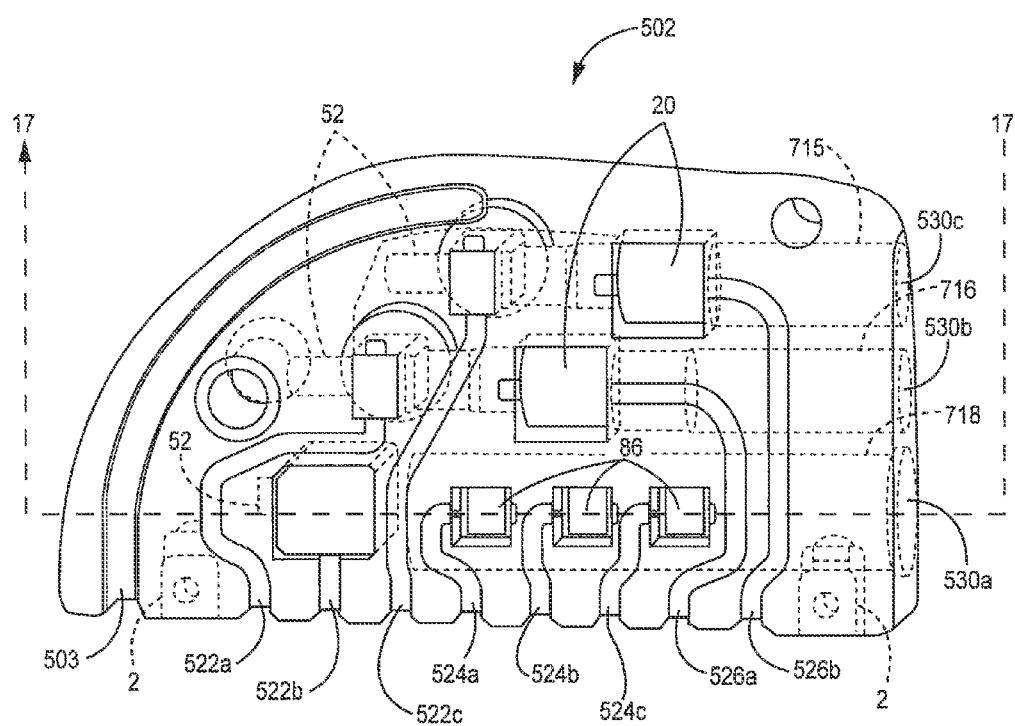
FIG. 17 is a plan view taken along lines 17-17 of a proximal lead connector assembly adapted for use with the stacked subassembly of FIGS. 16A-16B.

FIG. 17 is a plan view of a proximal lead connector assembly 50 adapted for use with the stacked subassembly 10 and shell 502 of FIGS. 16A-16B. Lead connector assembly 50 includes a pin connector terminal 52 and three ring connector terminals 54, 56, and 58 (shown in FIG. 1). Lead connector assembly 50 may generally correspond to an IS4 connector assembly, having four inline terminals 52, 54, 56 and 58, however, embodiments of the invention may be adapted for use with other lead connector assembly configurations such as a IS1. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, and 64. Lead connector assembly 50 can be an "in-line" connector assembly or a bifurcated connector assemblies which carry connector terminals on separate branches. In-line lead connector assemblies can have sealing rings along the insulating structures between connector terminals for providing a fluid resistant seal between circuit elements when the lead connector assembly is coupled to an implanted device. Medical electrical leads are positioned within substantially cylindrical bores, outlined in ghost lines, 715, 716, and 718. For example, atrial lead 715, right ventricular (RV) lead 716, and left ventricular (LV) lead 718 are shown positioned in the shell 502 such that the terminal pin 52 is coupled to a connector 20.

Figure 18:
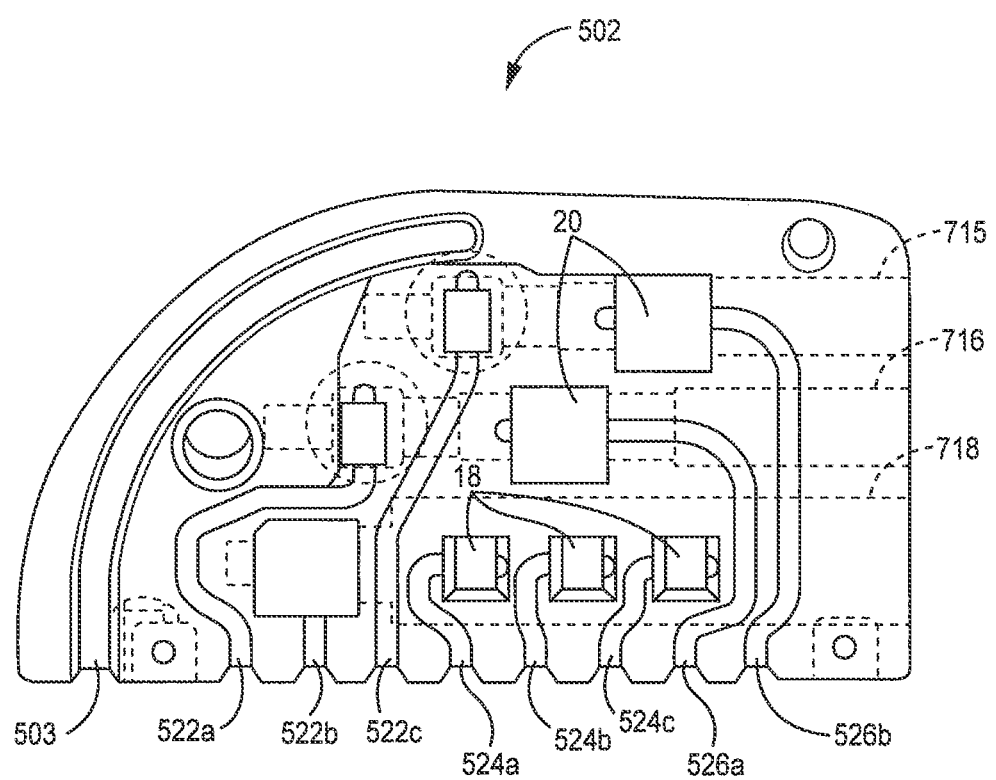
FIG. 18 is an enlarged perspective view of a connector shell including a set of apertures formed therein.

FIG. 18 is a perspective view of shell 502 and FIG. 4 is an end view of a connector assembly shell according to one or more embodiments of the invention. Shell 502 is formed during a single shot casting or molding process such as the exemplary description of how a molding process is performed is disclosed in U.S. Pat. No. 6,817,905 (Zart et al.), hereby incorporated herein by reference in its entirety; however, one or more embodiments of the present disclosure does not include the overmolding process that is disclosed in Zart. Shell 502 may be formed from a polymer, such as a polyurethane, and may thus be formed during high pressure and/or high temperature processes. Suitable polyurethane materials for forming shell 502 include a 75D polyurethane such as Thermedics™ Tecothane® available from Noveon, Inc., Cleveland, Ohio, or Pellethane™ available from Dow Chemical, Midland, Mich. Shell 502 is fabricated by loading a mandrel (not shown) in a mold into which the polymer material is applied. Shell 502 is thereby formed having an inner surface 82, which is formed by the mandrel, defining a connector bore 530*a*. Shell 502 may be additionally formed with channels 522, 524, 526, grooves, recesses or other features for receiving, retaining and/or aligning conductive traces of circuit member 90. In one or more embodiments, shell 502 is formed without a permanent metal molded therein. In one or more other embodiments, shell 502 may include embedded components or be formed with other additional features for receiving components during an assembly process, depending on the particular application. For example, the set screw block may be formed in shell 502.

Figure 19:
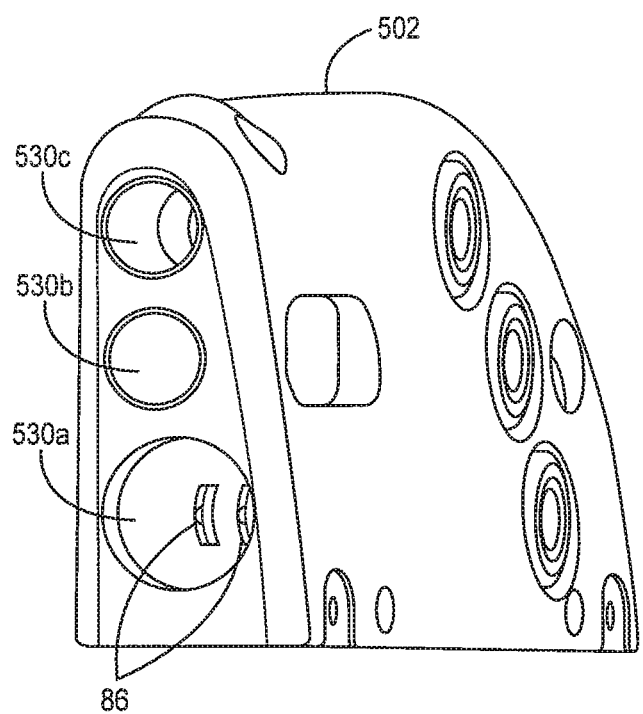
FIG. 19 is a perspective view taken of a connector shell including a set of apertures formed therein.

As shown in FIGS. 18 and 19, shell 502 includes connector bore 530*a*, however it is recognized that a connector shell 502 may be formed having multiple connector bore 530*a-c* to allow connection of more than one lead to the associated IMD. Shell 502 is formed having a plurality of apertures 86 (i.e. open windows) aligned with traces 92 extending from circuit member (i.e. hybrid board) (not shown). Apertures 86 become filled with conductive connectors 14, 16, and 18 provide access for electrically coupling traces 92 to connectors included in the stacked assembly 10 positioned in connector bore 530*c*. Shell 502 further includes a fill port (not shown) used for delivering an adhesive for creating a bond between shell inner surface 82 and sealing members included in a stacked subassembly inserted in connector bore 530*c*. An over fill port (not shown) is provided to allow excess adhesive and air bubbles to escape during the delivery process.

Figure 20A:
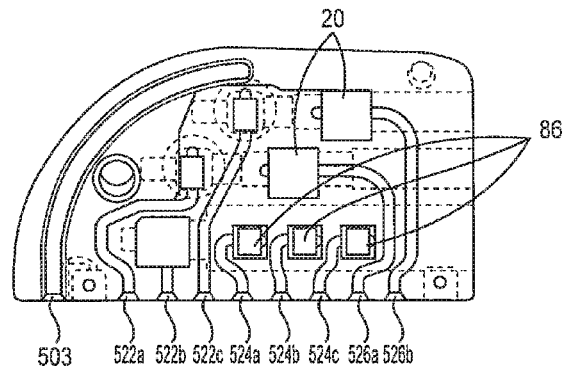
FIG. 20A depicts a molded shell that includes first and second ends with a bore extending therebetween.
Figure 20B:
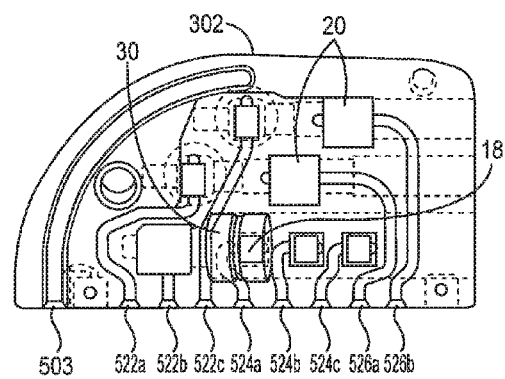
FIG. 20B depicts a molded shell after a first pair of members is inserted down the bore.
Figure 20D:
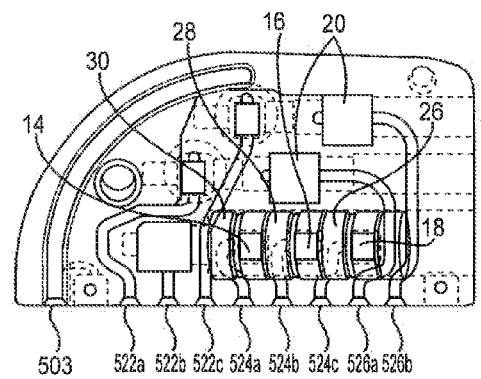
FIG. 20D depicts a molded shell after a third pair of members is inserted down the bore.
Figure 20C:
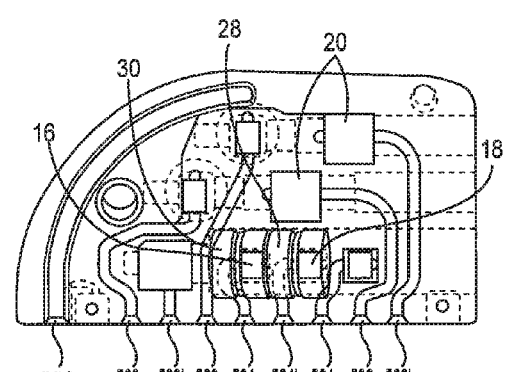
FIG. 20C depicts a molded shell after a second pair of members is inserted down the bore.
Figure 20E:
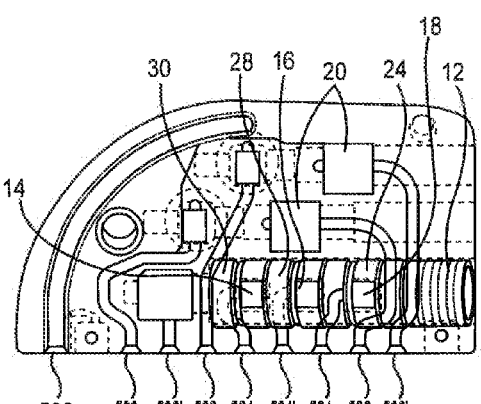
FIG. 20E depicts a molded shell after an end cap is inserted down the bore.
Figure 21:
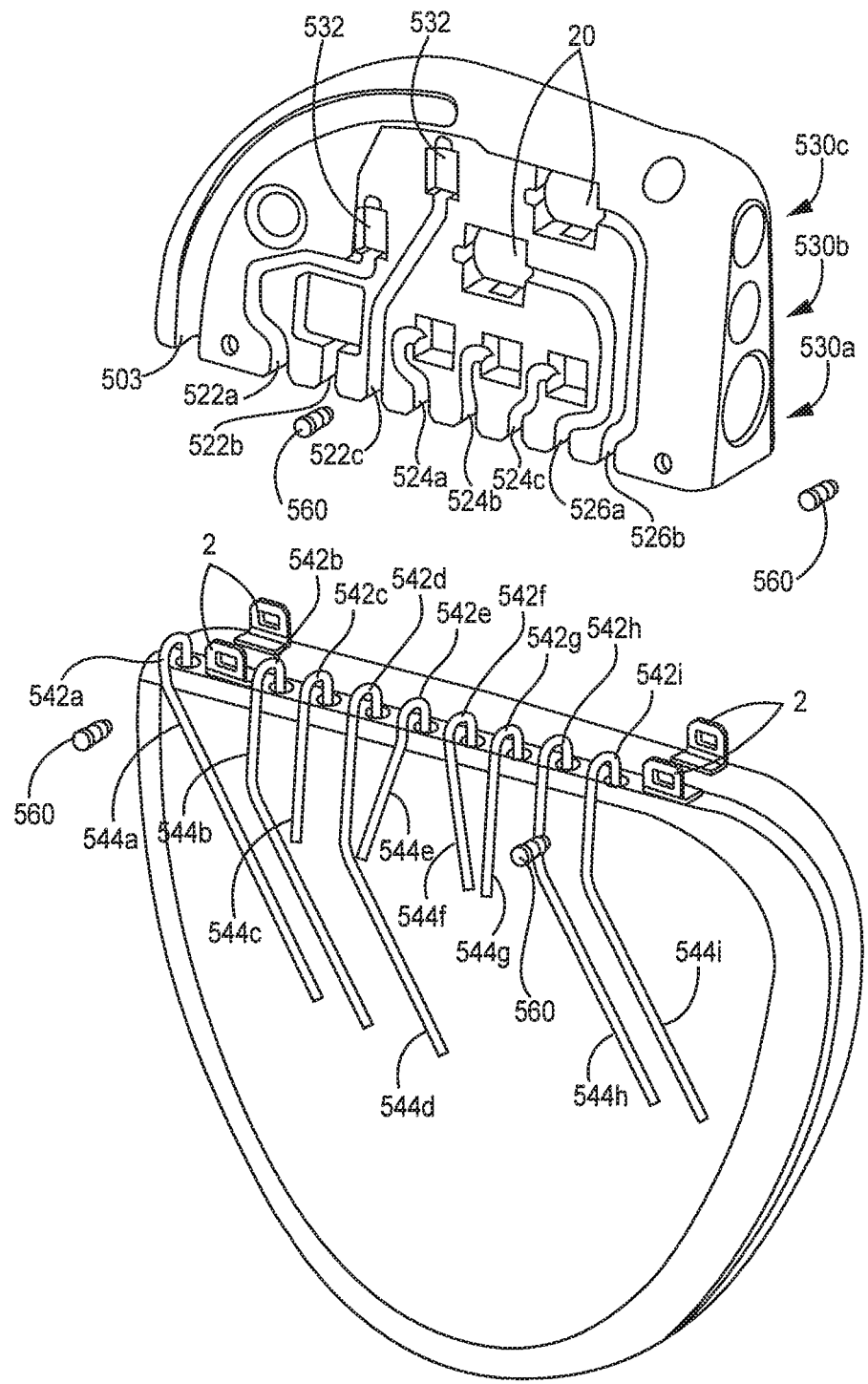
FIG. 21 is a perspective view of a connector assembly positioned over the can prior to the connector assembly being attached with pins to the can.
Figure 22A:
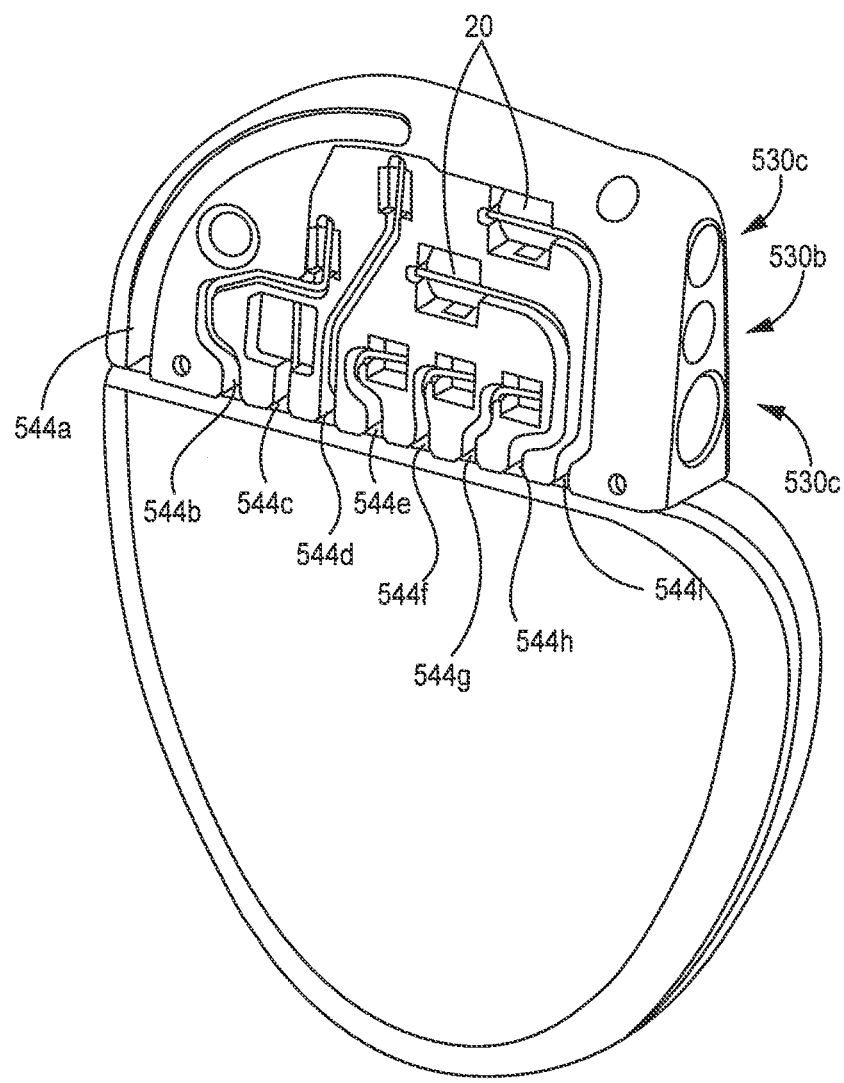
FIG. 22A is a perspective view of a device connector assembly including a molded shell and stacked subassembly inserted into the bore of the molded shell.
Figure 22B:
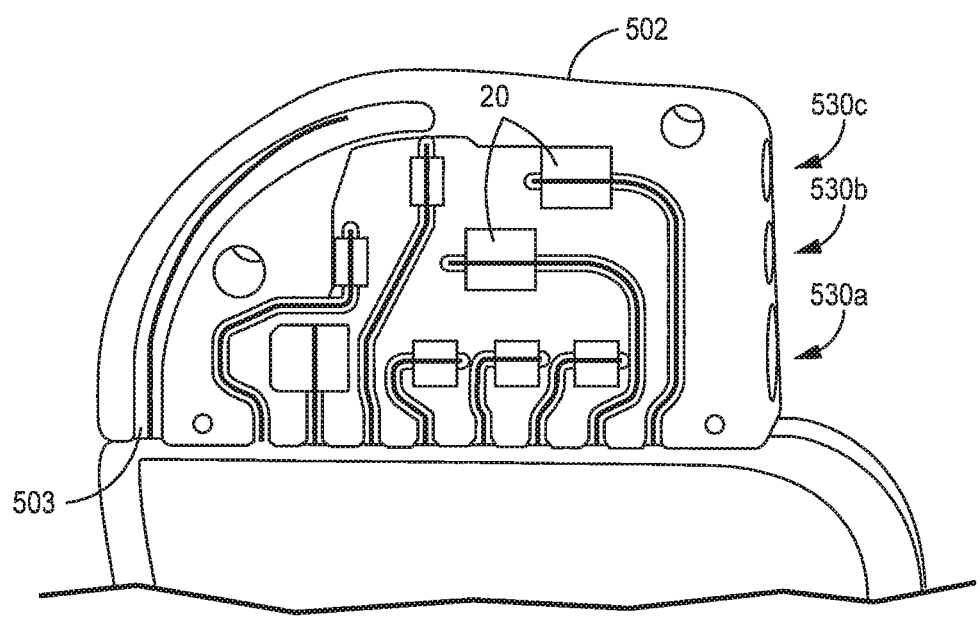
FIG. 22B is an enlarged perspective view of a device connector assembly including a molded shell and stacked subassembly inserted into the bore of the molded shell.
Figure 22C:
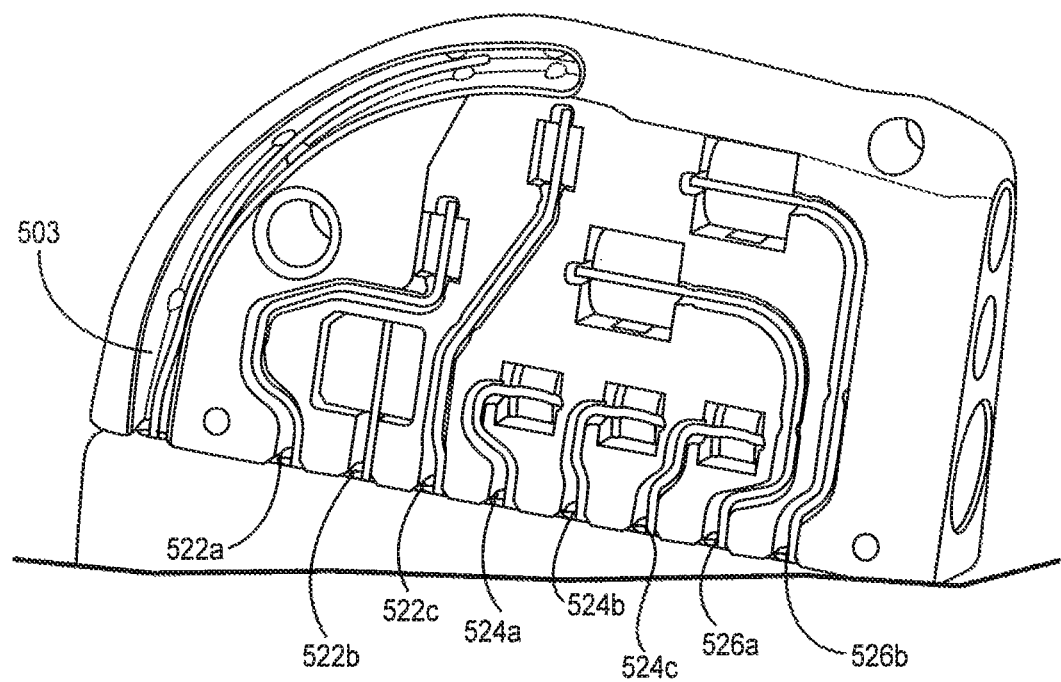
FIG. 22C is an enlarged perspective view of a device connector assembly including a molded shell and stacked subassembly inserted into the bore of the molded shell.

Referring to FIGS. 19-22, open windows or apertures 86 are molded into shell 502. The dimensions of each aperture is about 1 mm to about 5 mm with a depth of about 0.5 to about 5 mm. Open windows 86 are configured to receive connectors 14, 16, 18, which allow access for electrically coupling circuit member traces 92 to each of connector members 14, 16, 18. For example, as shown in FIG. 21-22, wires, feedthroughs or traces 542*a-g*, after insulative sleeves 544*a-i* are removed, maybe laser welded to connector members 14, 16, 18 through open windows 86. Windows 86 are subsequently filled with an insulating adhesive, such as silicone rubber to prevent ingress of body fluids around the circuit member connections. Alternatively, a conductive adhesive may be applied through windows 86 in order to electrically couple traces 92 to connector members 14, 16, 18 and set screw block 20. An insulating adhesive may then be applied over the conductive adhesive to seal windows 86.

In still another embodiment, traces 542*a-g* and connector members 14, 16, 18 are mechanically coupled to provide electrical connection between the traces and the connector members. For example, traces 542*a-g* may be pressed, staked, crimpled, or riveted to connector members 14, 16, 18 and 20 through windows 86. Any suitable method for electrically coupling traces 92 to connector members 14, 16, 18 may be used. Electrical connection of traces 542*a-g* with connector members 14, 16, 18 may occur before or after forming adhesive bonds.

With respect to routing wires through various channels and connecting wires to the conductive elements through windows 86, stacks 80, 502 may substantially ease the manufacturing process, which may improve quality due to the ease of manufacturing. For example, the first embodiment connector (FIGS. 1-15) is assembled over the wires that poke or extend through holes 88 (e.g. keyhole slot shown in FIG. 11A etc.) so that the connector could be assembled from top to straight down over the housing. One or more embodiments use the keyhole slots, such as that which is shown in FIGS. 11A-11B, as being used in place of the grooves shown in FIGS. 1, 3, and 7. As shown in FIGS. 11-12, the feedthrough comes out of the face of the device. Referring to FIG. 11A, the wires go through the holes loosely at first as the connector is assembled and then rotated into position. The access port allows the feedthrough or wires to project through and then the feedthrough wires are manually routed into the grooves. FIG. 12 shows the wires in place relative to stack 80 which includes skirt 89 or flange that hangs down away from the connector bore. The skirt is configured to strengthen and stiffen a joint which corresponds to the feedthrough shelf shown in FIG. 11A. The feedthrough exits from the side of the can onto a ledge or a feedthrough shelf shown in FIG. 11A.

Stack 502 also eases manufacturing of a connector module. Stack 502 lacks a skirt, whereas stack 80 clearly possesses skirt 89, as shown in FIG. 22. Stack 502, without the skirt to contact the feedthrough shelf, has increased physical packaging efficiency. FIG. 21 shows that the feedthrough or wires would actually be straight out and tilted out of the way so that operator can easily assemble the connector module. The feedthrough is shown to be located within the plane of the view rather than the feedthrough of stack 80, which is perpendicular to the plane of the view. As opposed to FIG. 12 which is parallel to the plane of the view and gets folded into recesses. Connectors 560 are pins that couple to fastener bracket 2.

Figure 23:
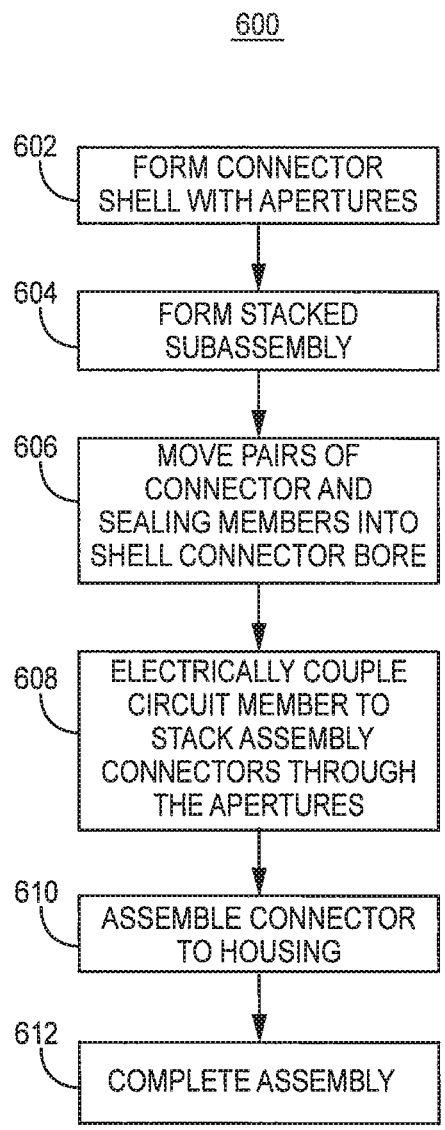
FIG. 23 is a flow chart for method of inserting a stacked assembly into a connector shell with a set of apertures that allows conductive connectors to be electrically connected with a feedthrough assembly.
Figure 24:
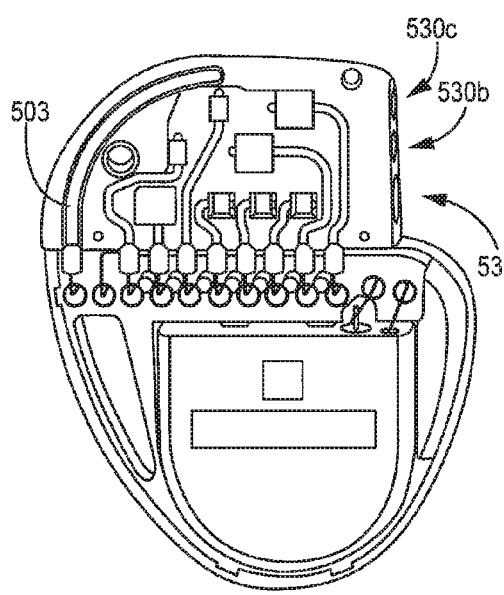
FIG. 24 is a top perspective views of the completed connector assembly coupled to an IMD.

The flow chart of FIG. 23 describes the formation of a connector assembly for use in an implantable medical device while FIGS. 20A-20E provide cross-sectional views of connector shell 502 as each operation is performed in order to form the connector assembly. Method 600 includes assembling a mandrel in a mold for forming a connector shell 502 at block 602. Typically, the shell is comprised of one or more polymer materials such as polyurethane in a high temperature, high pressure process. A shell inner surface 82 is formed by the mandrel defining a connector bore 530*a*. The connector shell 502 is molded using a one shot molding process. The one shot molding process employs one or more polymers used during a single run of the molding machine. In one or more embodiments, an overmold process is not used such as the overmold process described in U.S. Pat. No. 6,817,905 to Zart et al. to form the connector.

The molded shell, shown in FIG. 20A, includes first and second ends with a bore 530*a* extending between the first and second ends 510, 512. In one or more embodiments, the plurality of apertures 86 are radially disposed along the bore 530*a* and extend through the connector shell wall. The apertures 86 are spaced apart from each other. Apertures 86 serve the purpose of allowing the conductive lines or traces extending from a feedthough assembly to pass through the apertures 86 to the conductive connector members 14, 16, 18 of a stacked assembly 10.

The shell 502 may further include other features such as a fill port for injecting adhesive for bonding the shell inner surface 82 with the outer surface of sealing members positioned in the connector bore 530*a*, set screw apertures, and other features for accommodating additional connector bore 530*a* circuit members, connectors, or other components to be included in the connector assembly.

At block 608, a stacked subassembly is formed along the connector bore 530*a* by inserting a pair of members (sealing member and conductive member), as previously described. For example, after one pair is moved into its final position within bore 530*a* such that the conductive member has a surface exposed through an aperture, then another pair is moved down the bore 530*a*. The stacked subassembly is formed at block 610 by positioning a first pair (FIG. 20B), second pair (FIG. 20C), and third pairs (FIG. 20D), of conductive connector members 14, 16, and 18 interleaved with sealing members 24, 26, 28 along the connector bore 84 such that each conductive member is disposed within an aperture 86. End cap 12 is then inserted down the bore 530*a* as shown in FIG. 20E.

In one or more other embodiments, stacked subassembly 10 is separately formed and then inserted into bore 530*a*. For example, stacked subassembly 10 including sealing members, connectors and an end cap, which may be provided with interlocking features, are loaded onto an insertion tool 254. Using the insertion tool 254, the stacked subassembly is inserted into the shell connector bore 530*a*. Retention members (not shown) may be provided along the stacked subassembly outer diameter for engaging the shell inner surface 82 and securing the stacked subassembly 10 within the connector bore 530*a* upon full insertion. A second insertion tool may be used to compress the stacked subassembly within the connector bore 530*a*.

After the stack subassembly 10 is in position, at block 608, circuit member traces are electrically coupled to stack assembly 10 conductive connector members 14, 16, and 18 through the windows or apertures 86 that leaves a portion of the surface of the conductive connector members 14, 16, and 18 exposed. The exposed surface of the conductive connector member 14, 16, and 18 is electrically connected to the circuit through the traces 542*a*-*h*. Electrical coupling between circuit member traces and conductive connector members 14, 16, 18 may involve welding, or application of conductive adhesives. Electrical coupling between traces and connectors may additionally or alternatively include mechanical coupling between the traces and connectors involving riveting, staking, crimping or a protruding mechanical coupling member such as a spring, barb, button, or beam.

The connector assembly 550 is placed over the housing 552 (also referred to as the device case or can). In particular, the implantable medical device connector assembly 102 is secured to the housing 104.

Wires 46 are connected to cover 48. Cover 48 comprise the same or different conductive material as wire 46. Cover 48 is depicted as rectangular in shape but can be configured as any shape provided that cover 48 covers aperture 86. Wires 46 are routed via grooves 88 and the wire 46 is then welded (e.g. hot welded such as spot welded, cold welded) to wire 44. The connector assembly 102 is pinned in place to the housing 104 at block 610. Weld tab 2 helps to mechanically hold or secure the connector assembly 102 to the housing 104. The feedthrough wires are either brazed to feedthrough insulators 4 or glassed in. Feedthrough insulators 4 isolate the feedthrough wires electrically from the device case, while also providing a hermetic seal for IMD 100.

FIG. 21 is a cut-away perspective view of a device connector assembly including a molded shell 502 and stacked subassembly 10 formed down the bore 530*a* of the molded shell 502. As previously described, connector assembly 102 includes molded shell 502 formed during a molding process that includes windows or apertures 86 to allow circuit member traces to directly connect with conductive connector members of the stacked assembly 10. A stacked subassembly 10 is inserted into connector bore 530*a* having receptacle in end cap 12 for receiving a lead connector assembly. The stack assembly 10 may be inserted in sections (e.g. one or two pairs of seal members and conductive connector members) to better control the position of each contact. In an alternative embodiment, the stack assembly 10 can be pre-assembled and then positioned within bore 530*a* through a single insertion. Connector assembly 102 may further include one or more additional receptacles for receiving additional leads in one or more additional connector bore 530*a*. Connector assembly 102 includes a set screw aperture for receiving a set screw advanced into a set screw block positioned along connector bore 530*a*. Connector assembly 102 may include additional set screw apertures as needed for receiving additional set screws used for securing lead connector assemblies positioned in other connector bore 530*a*. Connector assemblies may alternatively be fabricated with other connectors in place of set screw blocks, such as spring connectors, for receiving lead connector pins, thereby eliminating the need for set screw apertures.

FIG. 22 is a perspective view of the completed connector assembly 102 shown in FIG. 21 coupled to housing 104 to form an IMD 400. IMD 400 may be a pacemaker, cardioverter/defibrillator, neurological stimulator, physiological monitor, or any other implantable medical device utilizing medical leads. In particular, sealing members are provided along a stacked subassembly 10 for creating a fluid-resistant seal with insulating portions of a lead connector assembly inserted into a receptacle. The sealing members also form a fluid-resistant interface with the inner surface of shell 86 along the outer surface of the sealing members. Stacked subassembly 10 is assembled with or without an insertion tool and inserted in connector shell 86 after shell 86 has been molded. The circuit member (also referred to as a hybrid board), partially embedded in connector shell (not shown), may be trimmed and electrically connected to internal circuitry enclosed in IMD housing. Electrical connection between IMD internal circuitry (not shown) and the circuit member is typically made via a feedthrough array extending through hermetically sealed housing.

Figure 25:
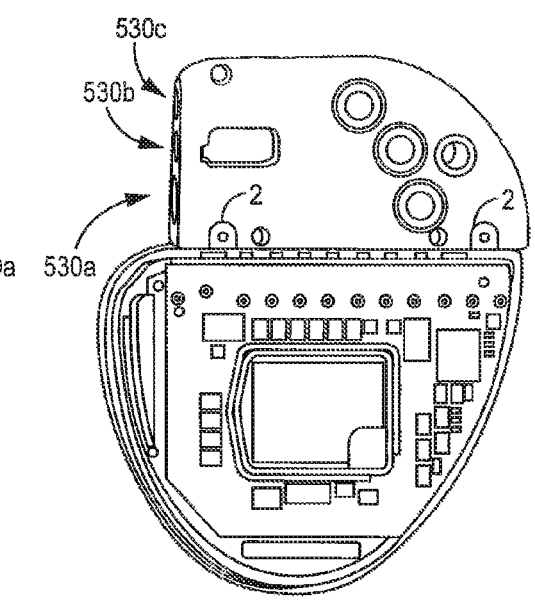
FIG. 25 is a bottom perspective view of the completed connector assembly coupled to an IMD.
Figure 26:
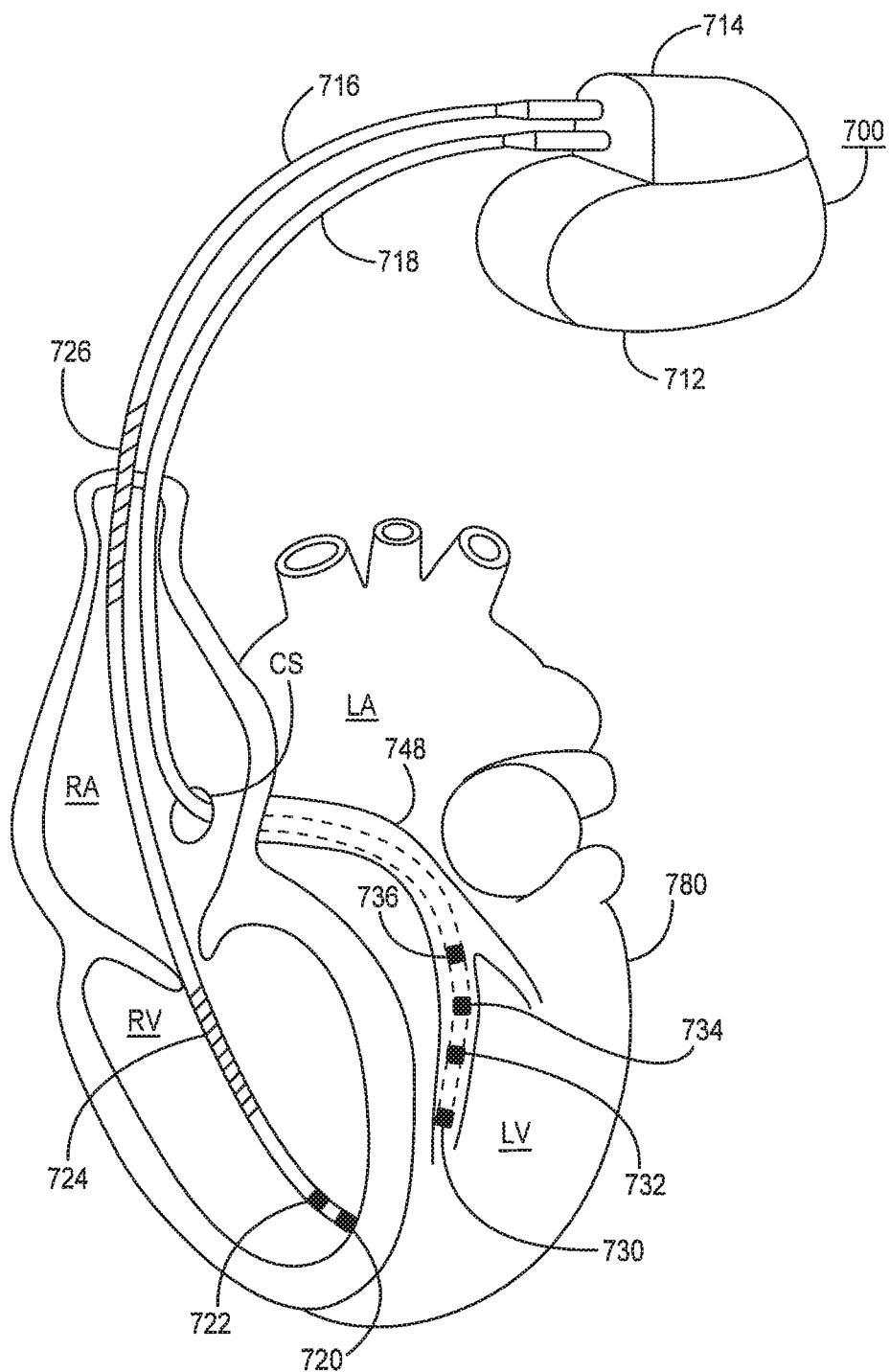
FIG. 26 depicts an IMD coupled to a patient's heart.

FIG. 25 depicts an implantable medical device (IMD) 700 coupled to a patient's heart 708 by way of a right ventricular (RV) lead 716 and a coronary sinus (CS) lead 18. An exemplary left ventricular lead with a set of spaced apart electrodes is shown in U.S. patent application Ser. No. 13/464,181 filed on May 4, 2012 by Ghosh et al., commonly assigned by the assignee of the present disclosure, the disclosure of which is incorporated by reference in its entirety herein.

The IMD 710 is embodied as a cardiac pacing device provided for restoring ventricular synchrony by delivering pacing pulses to one or both ventricles as needed to control the heart activation sequence. The heart 708 is shown in a partially cut-away view illustrating the upper heart chambers, the right atrium (RA) and left atrium (LA), and the lower heart chambers, the right ventricle (RV) and left ventricle (LV), and the great cardiac vein 748, which branches to form inferior cardiac veins. The great cardiac vein 748 opens into the coronary sinus (CS) in the right atrium.

The transvenous leads 716 and 718 connect IMD 710 with the RV and the LV, respectively. It is recognized that in some embodiments, additional leads and/or electrodes may be coupled to an IMD for connecting the IMD with the RA and the LA to provide sensing and/or pacing in three or all four chambers of the heart.

Each lead 716 and 718 carries pace/sense electrodes coupled to insulated, elongated conductors extending through leads 716 and 718. A remote indifferent housing electrode 712 is formed as part of the outer surface of the housing of the IMD 710. The pace/sense electrodes and the remote indifferent housing electrode 712 can be selectively employed to provide a number of pace/sense electrode combinations for pacing and sensing functions.

RV lead 716 is shown as a transvenous, endocardial lead passed through the RA into the RV. The RV lead 716 is formed with a proximal lead connector adapted for insertion into a connector bore of IMD connector block 714. Connector module 714, as illustrated, takes the form of an IS-4 quadrapolar connecter, but any appropriate connector mechanism may be substituted. The lead connector (not shown in FIG. 1) electrically couples electrodes 720, 722, 724, and 726 carried by RV lead 716 to internal circuitry of IMD 710 via connector block 714 such as the connector blocks using stack 80 or 502. RV pace/sense tip electrode 720 and proximal RV pace/sense ring electrode 722 are provided for RV pacing and sensing of RV EGM signals. RV lead 716 additionally carries an RV coil electrode 724 and a superior vena cava (SVC) coil electrode 726, which may be used for delivering high-voltage cardioversion or defibrillation shocks. RV ring electrode 22, RV coil electrode 724 or SVC coil electrode 726 are used in some embodiments as an anode paired with an electrode positioned along the LV for delivering unipolar pacing pulses in the LV during anodal capture analysis.

In the illustrative embodiment, a multi-polar LV CS lead 718 is passed through the RA, into the CS and further into a cardiac vein 48 to extend the distal four pace/sense electrodes 730, 732, 734 and 736 along the LV chamber to achieve LV pacing and sensing of LV EGM signals using any combination of electrodes 730 through 736. The LV CS lead 718 is coupled at a proximal end lead connector (not shown) inserted into a bore of IMD connector block 714 to provide electrical coupling of electrodes 730 through 736 to IMD internal circuitry. In other embodiments, the multi-polar lead 718 may include more than four electrodes or fewer than four electrodes. Any medical electrical lead configured to deliver multi-site pacing pulses to tissue can be employed to implement the methods described herein. An exemplary medical electrical lead can be the ATTAIN PERFORMA® LV lead, commercially available from Medtronic, PLC. located in Ireland.

Thus, an electrical medical device connector assembly incorporating a connector shell including a plurality of apertures (e.g. windows) configured to receive conductive connectors subsequently coupled to the hybrid board of the implantable medical device and an associated fabrication method have been presented in the foregoing description with reference to specific embodiments. It is appreciated that various modifications to the referenced embodiments may be made without departing from the scope of the invention as set forth in the following claims.

The invention claimed is:

1. A method for forming an implantable medical device including a connector assembly adapted to connect to a medical electrical lead, the method comprising:
providing a circuit member comprising electrical circuitry;
molding a shell having first and second opposing sides extending between first and second ends thereof, a bore being defined through at least one of the first and second ends of the shell to a bore distal end and a plurality of apertures being defined through at least one of the first and second sides of the shell and disposed along the bore;
forming a stacked subassembly along the connector bore, wherein forming the stacked subassembly comprises:
positioning a first pair of members comprising a first conductive member and a first sealing member along the connector bore, the first conductive member having a surface exposed through a first aperture of the plurality of apertures disposed in one of the first and second sides of the shell;
positioning a second pair of members comprising a second conductive member and a second sealing member along the connector bore, the second conductive member having a surface exposed through a second aperture of the plurality of apertures disposed in one of the first and second sides of the shell; and
coupling directly a plurality of conductive traces extending along at least one of the first and second sides of the shell from the circuit member through the first and second apertures to the first and second conductive members;
wherein the implantable medical device being a cardiac resynchronization therapy pacemaker.

2. The method of claim 1, wherein a plurality of channels are defined along at least one of the first and second sides of the shell, and further wherein coupling a plurality of conductive traces extending from the circuit member to the first and second conductive members comprises routing the plurality of conductive traces within the plurality of channels defined along at least one of the first and second sides.

3. The method of claim 1, wherein the method further comprises covering the plurality of apertures after coupling the plurality of conductive traces extending along at least one of the first and second sides of the shell from the circuit member to the first and second conductive members.

4. The method of claim 1 wherein the shell lacks a skirt.

5. The method of claim 1 wherein the first and second conductive members are not molded into the shell.

6. The method of claim 1 wherein the stacked subassembly being formed by positioning the first sealing member and the first conductive member together within the bore.

7. The method of claim 1 wherein the stacked subassembly being formed by positioning the second sealing member and the second conductive member together within the bore.

8. The method of claim 1 wherein a single shot operation is solely used to create the connector assembly.

9. The method of claim 1 wherein single bore for receiving a single medical electrical lead is solely formed in the connector assembly.

10. An implantable medical device connector assembly adapted to connect to a medical electrical lead, comprising:
a circuit member comprising electrical circuitry; a molded, insulative shell comprising first and second opposing sides extending between first and second ends thereof, a connector bore being defined through one of the first and second ends of the shell to a bore distal end by an inner surface of the shell, and further, a plurality of apertures being defined through at least one of the first and second sides of the shell and disposed along the bore;
a stacked subassembly positioned along the connector bore, the stacked subassembly comprising:
a first pair of members comprising a first conductive member and a first sealing member positioned together along the connector bore, the first conductive member having a surface exposed through an aperture of the plurality of apertures;
a second pair of members comprising a second conductive member and a second sealing member positioned together along the connector bore, the second conductive member having a surface exposed through an aperture of the plurality of apertures;
a first trace, extending from the circuit member, coupled to the first conductive member; and
a second trace, extending from the circuit member, coupled to the second conductive member;
wherein the implantable medical device being a cardiac resynchronization therapy pacemaker.

11. The implantable medical device connector assembly of claim 10, wherein a plurality of channels are defined along at least one of the first and second sides of the shell, and further wherein coupling a plurality of conductive traces extending from the circuit member to the first and second conductive members comprises routing the plurality of conductive traces within the plurality of channels defined along at least one of the first and second sides.

12. The implantable medical device connector assembly of claim 10, wherein the method further comprises covering the plurality of apertures after coupling the plurality of conductive traces extending along at least one of the first and second sides of the shell from the circuit member to the first and second conductive members.

13. The implantable medical device connector assembly of claim 10 wherein the shell lacks a skirt.

14. The implantable medical device connector assembly of claim 10 wherein the plurality of conductive members are not molded into the shell.

15. An implantable medical device comprising:
   a circuit member comprising electrical circuitry;
   a connector assembly adapted to connect to a medical electrical lead, the connector assembly comprising:
   a molded, insulative shell comprising first and second opposing sides extending between first and second ends thereof, a connector bore being defined through one of the first and second ends of the shell to a bore distal end by an inner surface of the shell, and further, a plurality of apertures being defined through at least one of the first and second sides of the shell and disposed along the bore;
   a stacked subassembly positioned along the connector bore, the stacked subassembly comprising:
   a first pair of members comprising a first conductive member and a first sealing member positioned together along the connector bore, the first conductive member having a surface exposed through a first aperture of the plurality of apertures disposed in one of the first and second sides of the shell;
   a second pair of members comprising a second conductive member and a second sealing member positioned together along the connector bore, the second conductive member having a surface exposed through a second aperture of the plurality of apertures disposed in one of the first and second sides of the shell;
   a first trace, extending from the circuit member, coupled to the first conductive member through the first aperture disposed in one of the first and second sides of the shell; and
   a second trace, extending from the circuit member, coupled to the second conductive member through a second aperture disposed in one of the first and second sides of the shell;
   wherein the implantable medical device being a cardiac resynchronization therapy pacemaker.

16. The implantable medical device of claim 15, wherein the connector assembly further includes a plurality of channels defined along at least one of the first and second sides of the shell, and further wherein coupling a plurality of conductive traces extending from the circuit member to the first and second conductive members comprises routing the plurality of conductive traces within the plurality of channels defined along at least one of the first and second sides.

17. The implantable medical device of claim 15, wherein the connector assembly further comprises covering the plurality of apertures after coupling the plurality of conductive traces extending along at least one of the first and second sides of the shell from the circuit member to the first and second conductive members.

18. The implantable medical device of claim 15, wherein the shell being without a skirt.

19. The implantable medical device of claim 15, wherein the first and second conductive members are not molded into the shell.

* * * * *